(12) United States Patent
Green et al.

(10) Patent No.: US 11,462,301 B2
(45) Date of Patent: Oct. 4, 2022

(54) SYSTEM AND METHOD FOR FLEET DRIVER BIOMETRIC TRACKING

(71) Applicant: BlyncSync Technologies, LLC, Broken Arrow, OK (US)

(72) Inventors: Austin Green, Fort Worth, TX (US); Steven Kastelic, Broken Arrow, OK (US)

(73) Assignee: BLYNCSYNC TECHNOLOGIES, LLC, Broken Arrow, OK (US)

( * ) Notice: Subject to any disclaimer, the term of this patent is extended or adjusted under 35 U.S.C. 154(b) by 912 days.

(21) Appl. No.: 15/615,005

(22) Filed: Jun. 6, 2017

(65) Prior Publication Data
US 2017/0351812 A1 Dec. 7, 2017

Related U.S. Application Data

(60) Provisional application No. 62/346,796, filed on Jun. 7, 2016.

(51) Int. Cl.
*G16B 40/20* (2019.01)
*G16H 40/67* (2018.01)
(Continued)

(52) U.S. Cl.
CPC ............. *G16B 40/20* (2019.02); *B60W 40/09* (2013.01); *B60W 50/14* (2013.01); *G06F 16/435* (2019.01); *G06N 3/02* (2013.01); *G16B 40/00* (2019.02); *G16H 40/67* (2018.01); *G16H 50/20* (2018.01)

(58) Field of Classification Search
CPC ........ G16B 40/00; G16H 40/67; G16H 50/20; G06F 16/435; B60W 40/09; B60W 50/14; G06N 3/02; A61B 5/4809; A61B 5/4806; A61B 5/4812
See application file for complete search history.

(56) References Cited

U.S. PATENT DOCUMENTS 9,486,027 B2 11/2016 Dey et al.
9,538,800 B2 1/2017 Dey et al.
(Continued)

OTHER PUBLICATIONS

Hokkanen et al, "Predicting sleep and lying time of calves with a support vector machine classifier using accelerometer data", 2011, Applied Animal Behavior Science, 134, pp. 10-15. (Year: 2011).*
(Continued)

*Primary Examiner* — Alexey Shmatov
*Assistant Examiner* — Clint Mullinax

(57) ABSTRACT

A method for employee biometric tracking is provided. The method comprises providing to a user a plurality of wearable devices capable of being connected to the user, establishing a wireless connection between the plurality of wearable devices and a mobile device, collecting by the plurality of wearable devices a plurality of biometric data from the user, receiving by an application stored on the mobile device the plurality of biometric data, inputting into a predictive engine biometric data selected from the plurality of biometric data, determining by the predictive engine in response to the biometric data whether the user is at, or soon will be at, an alert level, creating an alert signal, and displaying the alert signal to the user.

20 Claims, 13 Drawing Sheets

(51) Int. Cl.
*G16H 50/20* (2018.01)
*G06F 16/435* (2019.01)
*G16B 40/00* (2019.01)
*B60W 40/09* (2012.01)
*B60W 50/14* (2020.01)
*G06N 3/02* (2006.01)

(56) References Cited

U.S. PATENT DOCUMENTS

| | | | |
|---|---|---|---|
| 9,538,801 B2 | 1/2017 | Dey et al. | |
| 9,642,574 B2 | 5/2017 | Zhavoronkov et al. | |
| 9,686,136 B1 | 6/2017 | Dey et al. | |
| 9,955,450 B2 | 4/2018 | Dey et al. | |
| 10,383,384 B2 | 8/2019 | Zhavoronkov et al. | |
| 11,000,088 B2 | 5/2021 | Dey et al. | |
| 11,116,270 B2 | 9/2021 | Zhavoronkov et al. | |
| 2014/0221779 A1* | 8/2014 | Schoonover | A61B 5/38 600/27 |
| 2014/0249429 A1* | 9/2014 | Tran | A61B 5/0022 600/483 |
| 2014/0347265 A1* | 11/2014 | Aimone | H04W 4/029 345/156 |
| 2015/0015400 A1* | 1/2015 | Davis | G08B 21/06 340/575 |
| 2015/0302722 A1* | 10/2015 | Berezhnyy | A61M 21/00 340/565 |
| 2016/0090097 A1* | 3/2016 | Grube | A61B 5/18 340/576 |
| 2017/0112433 A1* | 4/2017 | Pugh | G01J 1/42 |
| 2018/0168265 A1 | 6/2018 | Sengupta et al. | |
| 2018/0249438 A1 | 8/2018 | Dey et al. | |
| 2019/0037954 A1 | 2/2019 | Friedman et al. | |
| 2019/0125026 A1 | 5/2019 | Friedman et al. | |
| 2019/0380417 A1 | 12/2019 | Zhavoronkov et al. | |
| 2020/0281298 A1 | 9/2020 | Dey et al. | |

OTHER PUBLICATIONS

Dawson et al, "Modelling fatigue and the of fatigue models in work settings", 2011, Accident Analysis & Prevention, vol. 43, Iss. 2, pp. 549-564. (Year: 2011).*

* cited by examiner

SYSTEM AND METHOD FOR FLEET DRIVER BIOMETRIC TRACKING

CROSS-REFERENCE TO RELATED APPLICATIONS

This application claims benefit of U.S. Provisional Application No. 62/346,796, filed Jun. 7, 2016, entitled SYSTEM AND METHOD FOR FLEET DRIVER BIOMETRIC TRACKING, the specification of which is incorporated by reference herein in its entirety.

BACKGROUND

Fatigued related crashes are well documented as a major problem within the trucking industry. There are many things that contribute to a driver's fatigue and there are plenty of wearable devices on the market. Currently, each device measures one or two specific biometrics. All current devices on the market are capable of short-range wireless communication. However, every device currently on the market only pairs with the smartphone through an application. Each device sends the data it collects to the application in an easy to read format. These devices only allow for a minimum amount of data collection for biometrics. Biometrics offer a wide range of measurements, but current devices contain very few data collection points. There are different wearables on the market that measure different biometrics ranging from voice recognition, speaker verification, facial/iris recognition, heartbeat/pulse recognition, body temperature, fitness, health, fatigue recognition, sweat hormone recognition, calories burned, distance traveled, steps taken, etc.

Within the trucking industry, they currently use paper logs for their drivers, these paper logs are supposed to record their driving times, sleep times, off time, and a few other details. Federal Motor Carrier Safety Administration is requiring all commercial freight transportation truck drivers to have electronic logs by the year 2018.

SUMMARY

In one aspect thereof, a method for employee biometric tracking is provided. The method comprises providing to a user a plurality of wearable devices capable of being connected to the user, establishing a wireless connection between the plurality of wearable devices and a mobile device, collecting by the plurality of wearable devices a plurality of biometric data from the user, receiving by an application stored on the mobile device the plurality of biometric data, inputting into a predictive engine biometric data selected from the plurality of biometric data, determining by the predictive engine in response to the biometric data whether the user is at, or soon will be at, an alert level, creating an alert signal, and displaying the alert signal to the user.

In another embodiment, the step of displaying the alert signal to the user further includes simultaneously displaying the alert signal to a remote management system.

In another embodiment, the method further comprises storing by the application and the remote management system an alert event, the alert event including biometric data that triggered the alert signal.

In another embodiment, the method further comprises training the predictive engine using the biometric data that triggered the alert signal, wherein the predictive engine is trained on data specific to the user.

In another embodiment, the method further comprises producing by the mobile device an audible alert simultaneously with displaying the alert signal to the user.

In another embodiment, the method further comprises producing by the mobile device a vibratory alert simultaneously with displaying the alert signal to the user.

In another embodiment, the plurality of biometric data includes at least one biometric data type.

In another embodiment, the alert level is a threshold value associated with the at least one biometric data type.

In another embodiment, the predictive engine is a neural network.

In another aspect thereof, a system for employee biometric tracking is provided. The system comprises a processor and a memory coupled to the processor, the memory containing computer executable instructions for establishing a wireless connection to a plurality of wearable devices, receiving a plurality of biometric data from the plurality of wearable devices connected to a user, inputting into a predictive engine biometric data selected from the plurality of biometric data, determining by the predictive engine in response to the biometric data whether the user is at, or soon will be at, an alert level, creating an alert signal, and displaying the alert signal to the user.

In another embodiment, the step of displaying the alert signal to the user further includes simultaneously displaying the alert signal to a remote management system.

In another embodiment, the memory further contains computer executable instructions for storing an alert event, the alert event including biometric data that triggered the alert signal.

In another embodiment, the memory further contains computer executable instructions for training the predictive engine using the biometric data that triggered the alert signal, wherein the predictive engine is trained on data specific to the user.

In another embodiment, the memory further contains computer executable instructions for producing an audible alert simultaneously with displaying the alert signal to the user.

In another embodiment, the memory further contains computer executable instructions for producing a vibratory alert simultaneously with displaying the alert signal to the user.

In another embodiment, the plurality of biometric data includes at least one biometric data type.

In another embodiment, the alert level is a threshold value associated with the at least one biometric data type.

In another embodiment, the predictive engine is a neural network.

BRIEF DESCRIPTION OF THE DRAWINGS

For a more complete understanding, reference is now made to the following description taken in conjunction with the accompanying Drawings in which.

DETAILED DESCRIPTION

Figure 1:
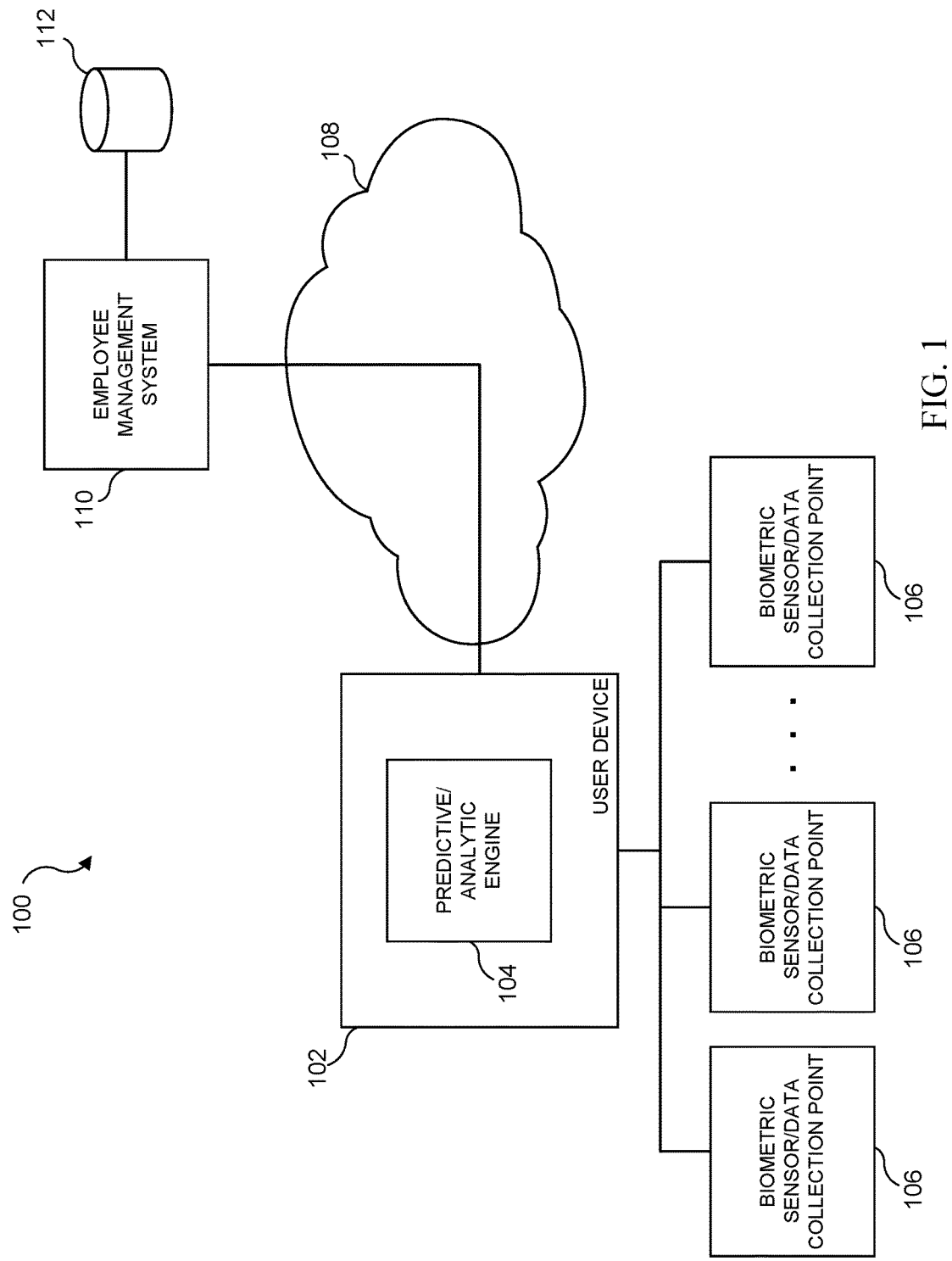
FIG. 1 illustrates a diagrammatic representation of one embodiment of a biometric tracking management system.

Referring now to the drawings, wherein like reference numbers are used herein to designate like elements throughout, various views and embodiments are illustrated and described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

With so many devices on the market only measuring one or two biometric points, these devices cannot alone truly predict or accurately measure the fatigue of a user, the level of sleep efficiency the user receives, and the level of fitness the user has. The software described herein not only takes data from every wearable as a center collection point but correlates all of the data and predicts the user's alertness, predicts the time of fatigue, and gauges sleep efficiency, fitness, and overall health. This is all done on an individual basis, meaning the predictions and final data will be learned on individual user averages. The data points are brought together through the individual user's mobile device and then sent to an employee manager's mobile device through their cellular signal.

All biometric sensors connect to the application through short-range wireless communication and allow for biometric predictive measures for the user. The software is open-ended allowing employee management platforms to connect the application directly into the employee management applications. The software also acts as an electronic log for the users, adding that much more benefit for the users and employee managers. With the data the application collects, it is able to plan trips and sleeping schedules for users. When planning activities such as driver routes, for example, employee managers or drivers can input destinations and dates, then the application automatically plans a sleep schedule for the driver.

When using Zigbee capable devices, each device has an IP address through the application and does not have to use any other connection platform like Bluetooth or infrared. This allows for a mesh network of biometrics around the user.

Referring now to FIG. 1, there is illustrated a diagrammatic representation of one embodiment of a biometric tracking management system 100. The system 100 includes a user device 102 having installed thereon a predictive/analytic engine 104 capable of receiving data on various biometrics of a user from a plurality of biometric sensors or data collection points 106. The plurality of biometric sensors or data collection points 106 may include any combination of biometric sensors for tracking the biometrics of a user, with each biometric sensor gathering one or more types of biometric data. The biometric sensors 106 may include and/or track pulse, accelerometer, thermometer, blink rate, finger print, facial recognition, DNA, palm print, hand geometry, iris recognition, retina, odor/scent, voice speaker recognition, thermograms, gait, ear recognition, skin reflection, lip motion, gyroscope, pulse oximeter, barometer, force touch, altimeter, GPS, and brain wave patterns. The system may also incorporate any future biometrics application to the user. All data, real-time, and predictive conclusions collected by the application may be encrypted so that only authorized users are able to access the data.

Examples of smart wearables containing the biometric sensors may include, but are not limited to, smart headsets, such as The Vigo and Maven Co-Pilot, fitness wristwatches, such as FitBit, Misfit Shine, Jawbone, Apple Watch, Pebble Time, Alcatel One Touch Watch, Moto 360, LG G Watch, Sony Smartwatch, Asus ZenWatch, Hauwei Watch, and Samsung Gear, and smart Hats such as the Smart Cap. These devices may be connected to the phone through a short range wireless frequency, that can range anywhere from but is not limited to Zigbee, Bluetooth, infrared, radio waves, cloud technology, thread, and any other connections existing now or in the future.

The mobile device 102 may be connected over a network 108 to an employee management system 110 that utilizes employee management hardware and software. The employee management system 110 may also have associated therewith a database 112 for use in storing system data and data on users, such as biometric data. Examples of employee management software the application may communicate with includes, but are not limited to, Fleet Locate by Spireon, FleetMatics REVEAL, Avrios, Horizon by Melton Technologies, Fleetio by Rarestep, GPS Insight Fleet Tracking Solution, Fleet Manager by GPSTrackIt, Fleet Commander by Agile Access Control, Verizon Networkfleet, CollectiveFleet by Collective Data, Fleetilla, ManagerPlus, Teletrac GPS Fleet Tracking, Omnitracs Roadnet Routing, RTA Fleet Management, GreenRoad, TomTom WEBFLEET, Vehicle Fleet Manager by Vinity Soft, Navistream by Streamline Transportation Technologies, and PeopleNet Fleet Manager.

It will be understood that the application of providing real time fatigue levels and predictions can apply to more than just the trucking industry. Fatigue monitoring and management can be relevant to a number of industries such as athletics, traveling, and long-term overnight shifts. In addition to fatigue levels, other conditions may be predicted or tracked, such as health conditions like a heart attack, psychological conditions like anxiety or depression, such as by tracking heart rate, brain wave patterns, etc., or overall health based on sleep patterns, exercise, etc.

Figure 2:
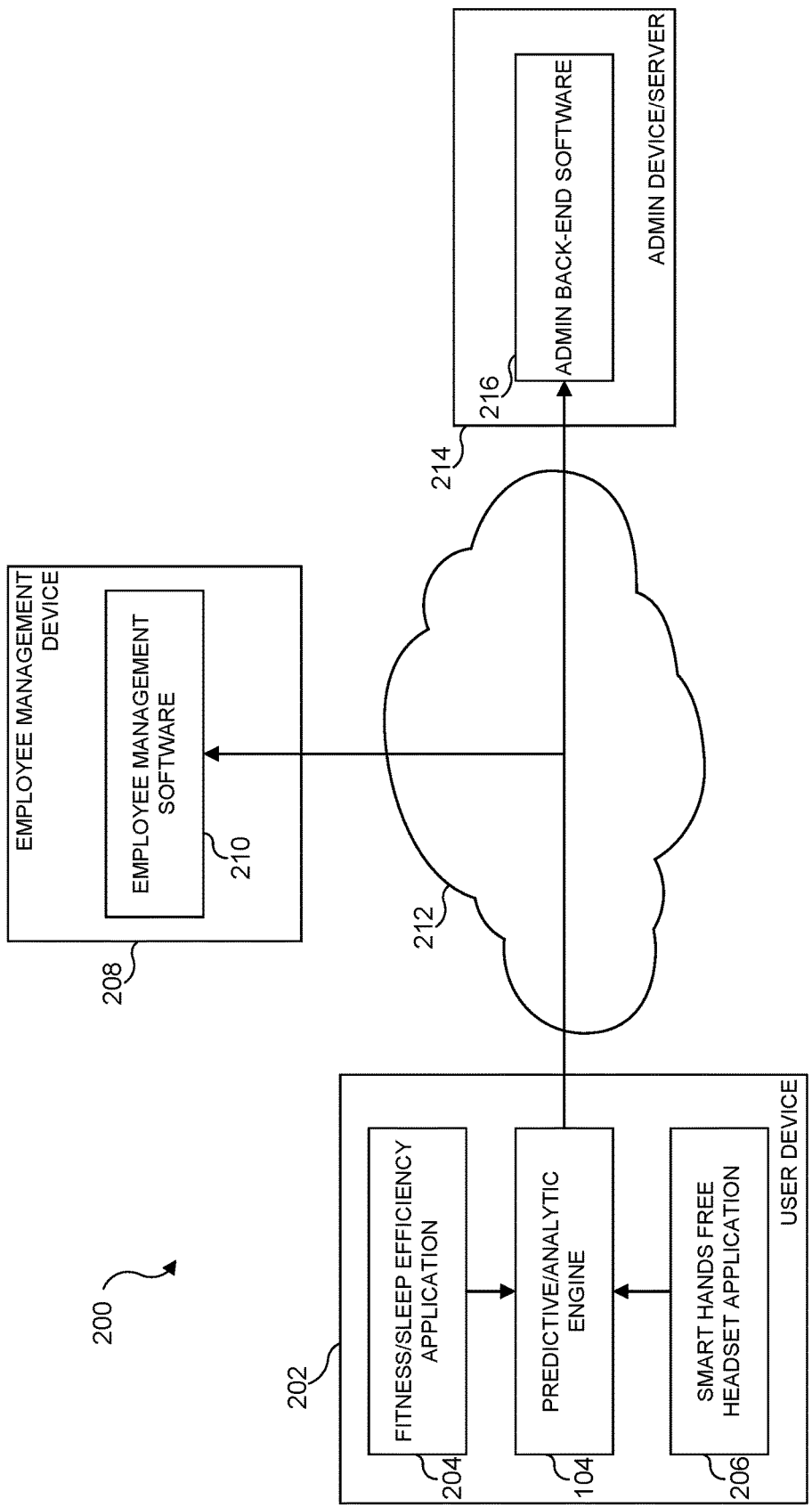
FIG. 2 illustrates a diagrammatic representation of one embodiment of a biometric tracking data flow system.

Referring now to FIG. 2, there is illustrated a diagrammatic representation of one embodiment of a biometric tracking data flow system 200. The system 200 includes a user device 202 having stored and running thereon a fitness/sleep efficiency application 204 and a smart hands free headset application 206. The fitness/sleep efficiency application 204 and the smart hands free headset application 206 receive biometric data from the user of the user device 202, such as a fleet driver, and the applications 204 and 206 pass this data into the predictive/analytic engine 104 also stored and running on the user device 202.

The biometric data collected by the fitness/sleep efficiency application 204 comes from sensors built into its corresponding fitness wristwatch hardware. Examples of fitness smart band hardware include but are not limited to FitBit, Misfit Shine, IHealth, Jawbone, and PulseBand. This hardware is capable of biometric sensors such as pulse rate, body temperature, calories burned, steps taken, distance traveled, accelerometer, gyroscope, and more. The biometric data collected by the smart hands free headset application 206 is taken from sensors built into its corresponding smart hands free hardware. Examples of this hardware include but are not limited to The Vigo Headset, or The Maven Co-Pilot. This hardware is capable of sensing biometrics such as facial recognition, blink rate, gyroscopic head tilt, yawn detection, and more. Headsets such as these may also be designed, for example, to audibly alarm a driver who is nodding off at the wheel.

The predictive/analytic engine 104 simultaneously collects data from the fitness/sleep efficiency application 204 and the smart hands free headset application 206 in real time. The engine 104 is able to reproduce and display the same data received from the fitness/sleep efficiency application 204 and the smart hands free headset application 206, and may also display a predictive conclusion of the time the user can expect to feel fatigued. The conclusion becomes more accurate over time as the user continues to use the engine 104 and the engine 104 learns the user's sleeping and fatigue behaviors. The engine 104 may also simultaneously display electronic log information in real time, as biometric data received from the applications 204 and 206 can be aggregated to display a user's active working time, rest or break time, off-duty time, sleep time, etc.

The system 200 further includes an employee management device 208 having stored and running thereon employee management software 210. The employee management device 208 may be any computing device capable of running the employee management software 210. The employee management software 210 receives data from the predictive/analytic engine 104 over a network 212. The conclusion provided by the predictive/analytic engine 104 may be displayed in real time on the employee management device 208 after being received by the employee management software 210. The predictive/analytic engine 104 may also provide the employee management device 208 access to the biometric data received from the fitness/sleep efficiency application 204 and the smart hands free headset application 206 at any time. Managers may also be able to view each individual user's log time via information received by the employee management device 208. Examples of employee management software include but are not limited to People-Net, Verizon Networkfleet, FleetMatics, RareStep Fleetio, and Spireon FleetLocate.

The system 200 further includes an admin device/server 214 having stored and running thereon admin back-end software 216. The admin back-end software 216 allows for administrators or developers of the predictive/analytic engine 104 software to view activity and data from all users running a copy of the predictive/analytic engine 104. The admin back-end software 216 also has the ability to terminate the operation of any individual predictive/analytic engine 104.

Figure 3:
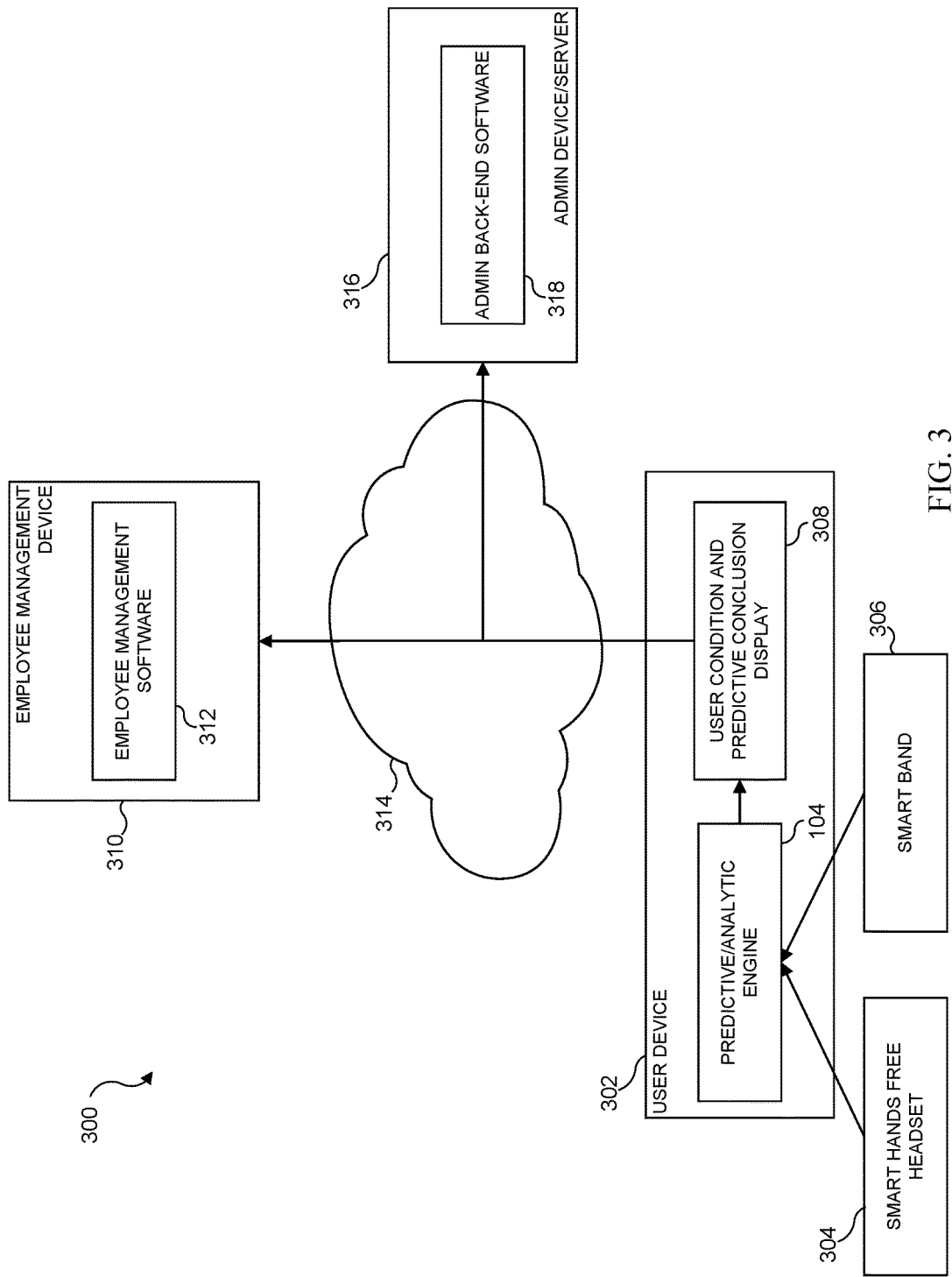
FIG. 3 illustrates a diagrammatic view of another embodiment of a biometric tracking data flow system.

Referring now to FIG. 3, there is illustrated a diagrammatic view of another embodiment of a biometric tracking data flow system 300. The system 300 includes a user device 302 having stored and running thereon the predictive/analytic engine 104. The predictive/analytic engine 104 receives biometric data directly from a plurality of wearables, such as a smart hands free headset 304 or a smart band 306, through each respective wearable's application program interface (API). This also allows for raw data to be viewed, accessed, or manipulated before it is run through the predictive engine. Examples of fitness smart band hardware include but are not limited to FitBit, Misfit Shine, IHealth, Jawbone, and PulseBand. This hardware is capable of biometric sensors such as pulse rate, body temperature, calories burned, steps taken, distance traveled, accelerometer, gyroscope, and more. Examples of smart hands free headset hardware include but are not limited to The Vigo Headset, or The Maven Co-Pilot. This hardware is capable of sensing biometrics such as facial recognition, blink rate, gyroscopic head tilt, yawn detection, and more. Headsets such as these may be designed, for example, to audibly alarm a driver who is nodding off at the wheel.

The predictive/analytic engine 104 simultaneously collects data from the plurality of wearables in real time. The engine 104 is able to manipulate and display the biometric data received from the plurality of wearables, and may also display a predictive conclusion of the time the user can expect to feel fatigued. The conclusion and other data may be displayed on the user device 302 on a user condition and predictive conclusion display 308. The display 308 may include information such as the user's fatigue level, user sleep efficiency, user physical and emotional health conditions, and/or other conditions. The display 308 may be standardized so that similar information is formatted and displayed in a similar way every time the display 308 is updated. The conclusion becomes more accurate over time as the user continues to use the engine 104 and the engine 104 learns the user's normal conditions and behaviors. The engine 104 may also simultaneously display electronic log information in real time, as biometric data received from the plurality of wearables can be aggregated to display a user's active working time, rest or break time, off-duty time, sleep time, etc.

The system 300 further includes an employee management device 310 having stored and running thereon employee management software 312. The employee management device 310 may be any computing device capable of running the employee management software 312. The employee management software 312 receives data from the predictive/analytic engine 104, which may include the same display 308, over a network 314. The conclusion provided by the predictive/analytic engine 104 may be displayed in real time on the employee management device 310 after being received by the employee management software 312. The predictive/analytic engine 104 may also provide the employee management device 310 access to the biometric data at any time. Managers may also be able to view each individual user's log time via information received by the employee management device 310. Examples of employee management software include but are not limited to People-Net, Verizon Networkfleet, FleetMatics, RareStep Fleetio, and Spireon FleetLocate.

The system 300 further includes an admin device/server 316 having stored and running thereon admin back-end software 318. The admin back-end software 318 allows for administrators or developers of the predictive/analytic engine 104 software to view activity and data from all users running a copy of the predictive/analytic engine 104. The admin back-end software 318 also has the ability to terminate the operation of any individual predictive/analytic engine 104.

Figure 4:
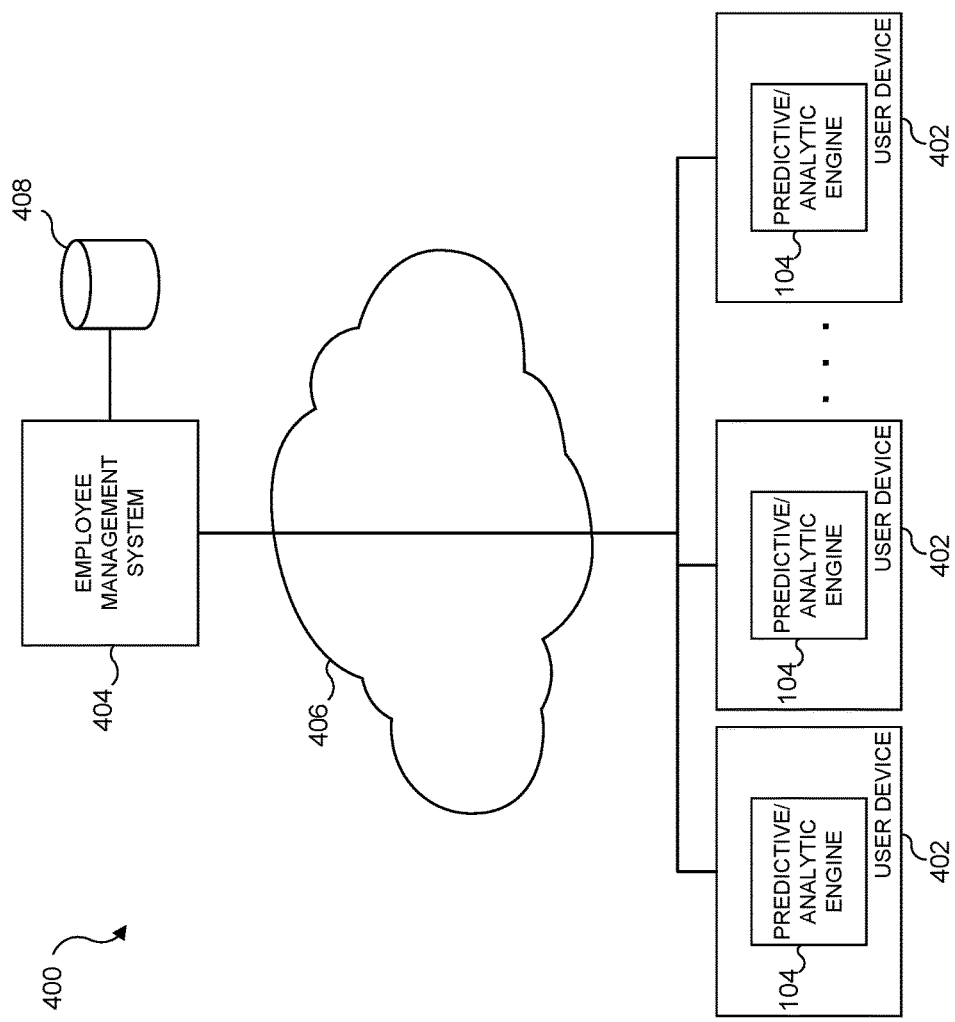
FIG. 4 illustrates a diagrammatic view of one embodiment of a multiple user biometric tracking management system.

Referring now to FIG. 4, there is illustrated a diagrammatic view of one embodiment of a multiple user biometric tracking management system 400. The system 400 includes a plurality of user devices 402 having stored and running thereon copies of the predictive/analytic engine 104. The plurality of user devices 402 communicate with an employee management system 404 over a network 406. The employee management system 404 may register multiple users of the predictive/analytic engine 104, and may access all data or predictive conclusions that is stored on or presented by each one of the plurality of user devices 402.

The plurality of user devices 402 provide to the employee management system 404 biometric data on each user of each one of the plurality of user devices 402, predictive conclusion displays, fatigue alerts for each user of each one of the plurality of user devices 402, electronic logs of each user of each one of the plurality of user devices 402, and other information. This information may be responded to by the employee management system 404 when needed. This information may also be stored by the employee management system 404 in a database 408, the database 408 providing relationships between users' biometrics, alert levels, fatigued statuses, electronic log information, and other tracked data. At any time throughout the day, managers have the capability to access the raw data timelines as well as the predictive real-time conclusions of their registered users. Whenever a user is audibly alarmed of medium or high alert levels, the managers also receive a notification at the same time. The managers can also be provided with simple monitoring software so they can see all their employee's fatigue information, or such can be integrated into already existing employee management systems such as PeopleNet or Verizon NetworkFleet, providing fatigue data alongside the truck data they already collect.

Figure 5:
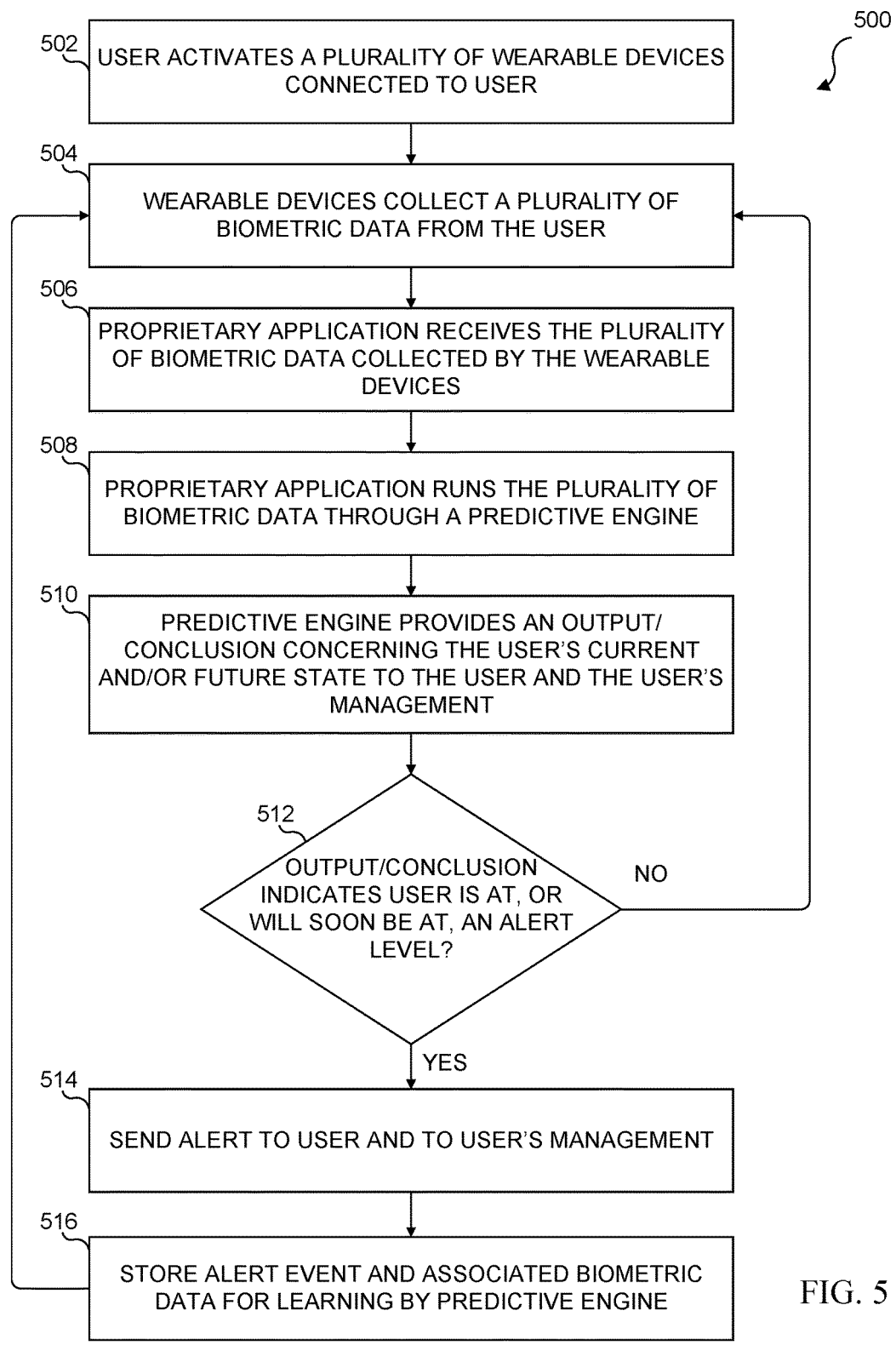
FIG. 5 illustrates a flowchart of one embodiment of a user biometric tracking and alert process.

Referring now to FIG. 5, there is illustrated a flowchart of one embodiment of a user biometric tracking and alert process 500. The process 500 begins at step 502 where a user activates a plurality of wearable devices worn by or otherwise connected to the user. The wearable devices may be any type of wearables such as the wearables described herein. At step 504, the plurality of wearable devices collect a plurality of biometrics from the user, the specific biometrics being any type of biometric as described herein. At step 506, a proprietary application, such as the predictive/analytic engine 104, receives the plurality of biometric data collected by the plurality of wearable devices. The proprietary application, as described herein, may receive the biometrics from the plurality of wearable devices directly, or may receive the biometrics by interfacing with other applications that gather biometrics from the plurality of wearables.

At step 508, the proprietary application runs the plurality of biometric data through a predictive engine. As described herein, the predictive engine may be a trained neural network, with the biometrics acting as inputs into the neural network to predict a result. The predictive engine may also be a linear, threshold-driven, predictive engine. In embodiments where the predictive engine is driven by thresholds, particular thresholds may be set in the proprietary application for specific biometrics, or even thresholds for combinations of biometrics. These thresholds may change over time for each individual user, as the proprietary application gathers more data on the user. For instance, if a particular threshold is set for a biometric, such as heart rate, the threshold may be reached by a user even though the user has not reached a dangerous state, but rather simply has a faster or slower heart rate than average. If that is the case, the threshold may be adjusted. This may be automated, or the user may input into the system, upon being alerted of a dangerous condition, that there is no cause for alarm. This input by the user may have to be approved by the user's manager, to avoid abuse by the user. The threshold would then be adjusted for that user.

At step 510, the predictive engine provides an output or conclusion concerning the user's current and/or future state, providing the output to the user and the user's manager or central office. At decision block 512, it is determined whether the output or conclusion generated by the predictive engine indicates that the user is at, or will soon be at, an alert level. This, again, can be determined by the trained neural network or a threshold-driven system. If it is determined that the user is not at an alert level, the process 500 moves back to step 504, where the devices continue to collect biometric data from the user. If it is determined that the user is at an alert level, the process 500 moves to step 514 where an alert is sent to the user and the user's manager. This alert may be an alarm that wakes a user up, or some other notification that, for example, may tell the user to stop what he is doing or pull a vehicle over if the alert is regarding a dangerous condition, such as a heart attack. It may also be at this time that the user inputs that there is no need for the alert. Alerts will only be sent to the user and the manager when one or more biometric is crossing the predetermined outlying threshold while the user is awake. Conclusions (such as predicted time to feel fatigued, sleep efficiency, health/fatigue levels, and sleep management) are accessible at any time. Real-time raw data, displayed over a timeline, will also be accessible at any time. The process then moves to step 516, where the alert event and the biometric data associated with the alert event, that is, the biometric data that triggered the alert, is stored so that the predictive engine may be adjusted for that user, if needed. The process then moves back to step 504 to continue collecting biometric data from the user.

Figure 6:
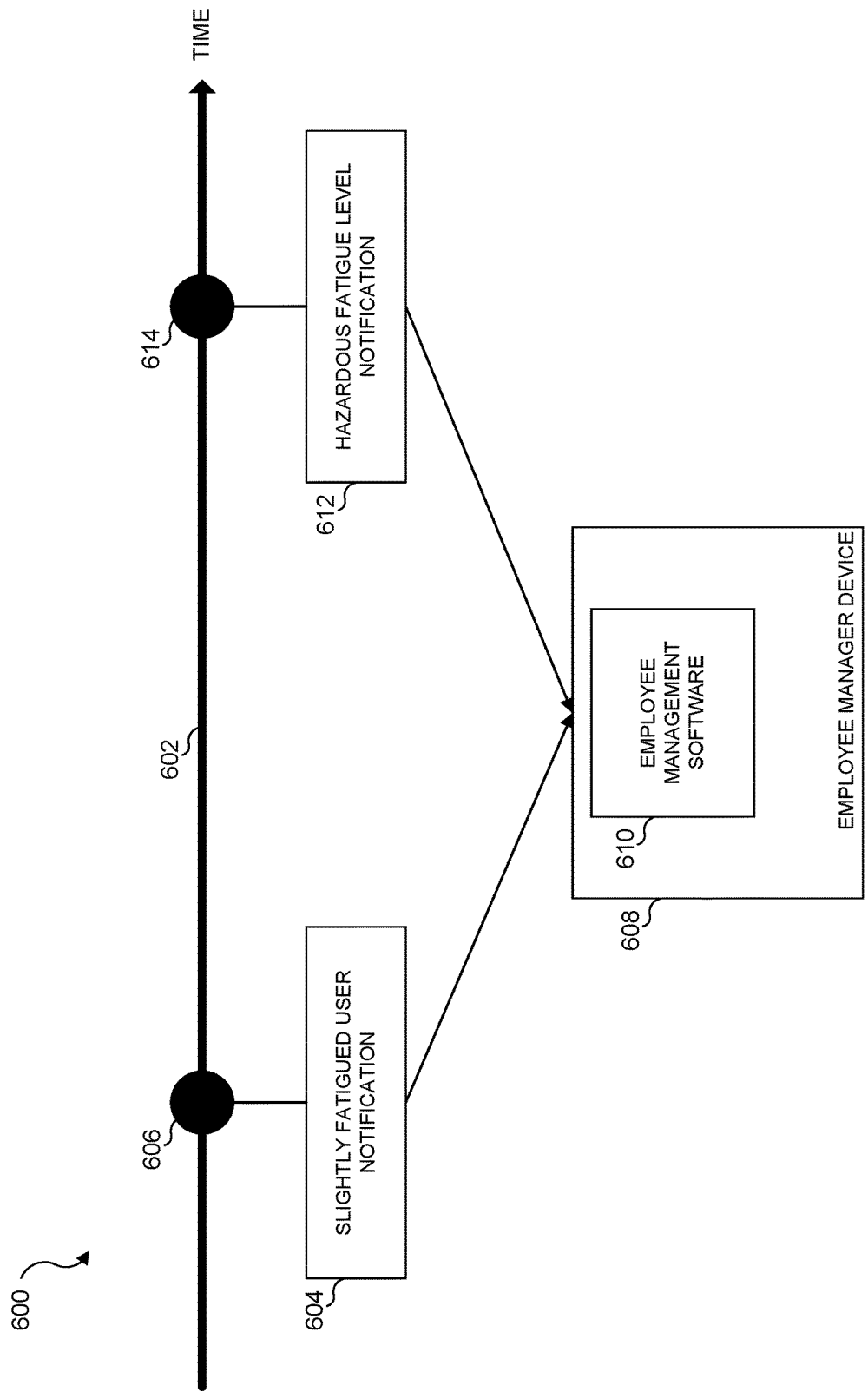
FIG. 6 illustrates a diagrammatic view of one embodiment of a fatigue alert process.

Referring now to FIG. 6, there is illustrated a diagrammatic view of one embodiment of a fatigue alert process 600. A proprietary application tracks a user's biometrics over a period of time 602. A fatigue notification 604 may be triggered at a point in time 606 when the user is expected to begin to feel fatigued. The point in time 606 is predicted by the proprietary application based on a default setting, which may be adjusted based on the user's biometrics and actual fatigue patterns gathered over time. The fatigue notification 604 may be sent to an employee manager device 608 having stored and running thereon employee management software 610 immediately when the point in time 606 is reached. The fatigue notification 604 may also be sent immediately upon detection of a fatigued state even if before the point in time 606.

The fatigue notification 604 may differ in content and appearance when a fatigued status is merely expected versus when a fatigued status is detected by the proprietary software. For example, if the point in time 606 is reached, but no actual fatigue state or other hazardous state is detected, the fatigue notification 604 may simply indicate that the user is now expected to be feeling fatigued, which may only serve to alert the user and the manager that the user should soon consider taking a break. If the fatigue notification 604 is however triggered by the detection of a fatigued state, the fatigue notification 604 may indicate a more severe warning and may instruct the user and the manager that the user should now take a break or give an amount of time in which to take a break. In some cases, the fatigue notification 604 may provide an audible alert or other type of alert such as a vibration to the user, if the readings indicate certain conditions, such as an indication that the user is nodding off or becoming less focused due to blink rate and head movement.

Similarly, a hazardous fatigue notification 612 may be triggered at a point in time 614 when a user is expected to be fatigued to the point of continued operation being hazardous to the user or others. The point in time 614 may be predicted by the proprietary application based on a default setting, which may be adjusted based on the user's biometrics and actual fatigue patterns gathered over time. The hazardous fatigue notification 612 may be sent to the employee manager device 608 immediately when the point in time 614 is reached. The hazardous fatigue notification 612 may also be sent immediately upon detection of a hazardous fatigue state, or any other hazardous state, even if before the point in time 614.

The hazardous fatigue notification 614 may differ in content and appearance when a hazardous fatigue status is merely expected versus when a hazardous status is detected by the proprietary software. For example, if the point in time 614 is reached, but no actual fatigue state or other hazardous state is detected, the notification 612 may simply indicate that the user is now expected to be feeling dangerously fatigued, which may only serve to alert the user and the manager that the user should take a break or get some sleep. If the notification 612 is however triggered by the detection of a hazardous state, the notification 612 may indicate a more severe warning and may instruct the user and the manager that the user should immediately cease operation at the next safe opportunity. In some cases, the notification 612 may provide an audible alert or other type of alert such as a vibration to the user, if the readings indicate certain conditions, such as an indication that the user is nodding off due to blink rate and head movement.

Figure 7:
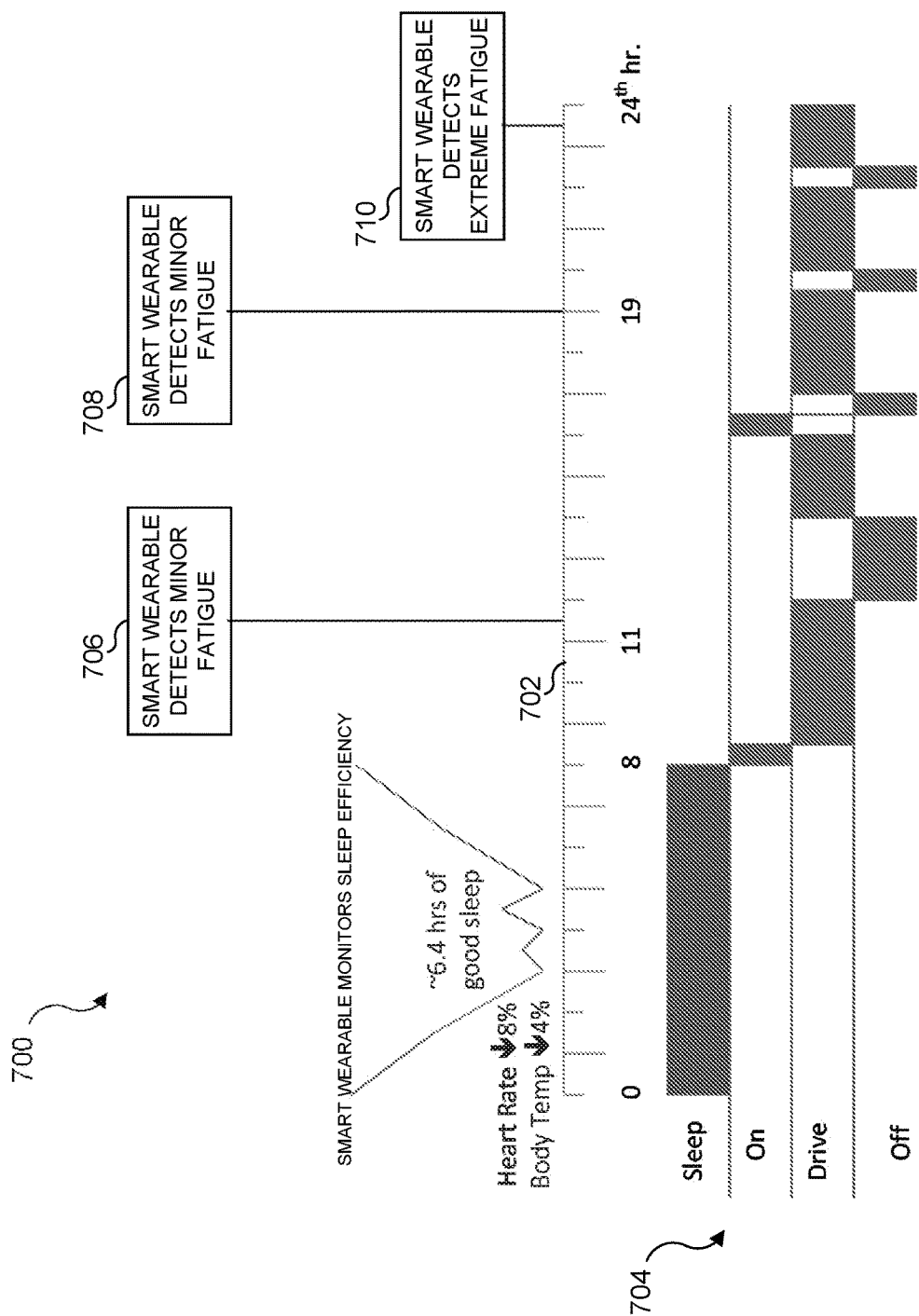
FIG. 7 illustrates a diagrammatic view of one embodiment of a user biometric tracking, fatigue alert, and electronic log diagram.

Referring now to FIG. 7, there is illustrated a diagrammatic view of one embodiment of a user biometric tracking, fatigue alert, and electronic log diagram 700. The diagram 700 includes a timeline 702 which shows a 24-hour period during which a user's biometrics are tracked. Tracked biometrics are gathered and monitored by a proprietary application in order to prepare conclusions of real-time fatigue level display and predictions, such as that described herein. Below the timeline 702 is an electronic log 704 indicating various states of the user at various point on the timeline 702. The electronic log 704 may adhere to industry regulations such as trucking industry regulations concerning electronic logs. The electronic log 704 may be updated automatically in real time as the user's biometrics are tracked, and may be viewed by the user, employee management, and admins or developers of the proprietary application. In this embodiment, the electronic log 704 includes four different states: "Sleep," "On," "Drive," and "Off." The "Sleep" state indicates when the user is actively sleeping, as may be detected by wearables or indicated by the user. During sleep, the user may only wear a smart watch or smart band that may track multiple biometrics. In the example shown in diagram 700, the user is asleep for the first eight hours of the timeline 702. During this eight-hour sleep period, there is shown that the wearables indicate that the user's heart rate dropped 8% and the user's body temperature dropped 4%. The wearables also track the number of hours of "good sleep" wherein in the example shown in diagram 700, was about 6.4 hours. Such "good sleep" may be indicated by a number of factors, such as the aforementioned heart rate and body temperature, or amount of movement, such as tossing and turning or getting out of bed.

The "On" state of electronic log 704 indicates times when the user is actively working or "on the job" but is not currently driving, while the "Drive" state indicates when the user is driving. In other embodiments, the "Drive" state may be another active working status, such as "Working," "On A Call," "In Assembly Line," or other statuses. In other embodiments of an electronic log, the electronic log may show both the "On" state and the "Drive" state at the same time, for those time periods where the user is both on the job and driving. While in the "On" and "Drive" states, the user may wear and/or connect additional wearables in addition to smart bands or watches, such as a smart headset. As the user turns on more wearables throughout the day, the proprietary application may automatically maintain a short-range wireless connection to each wearable. The "Off" state is the state during which the user is "off the job," i.e., not driving and taking a break, sleeping, or otherwise not working.

The diagram 700 further illustrates on the timeline 702 when fatigue detection occurs from the combination of sensors monitoring the user's biometrics. In the example shown in diagram 700, a first minor fatigue detection 706 occurs at around the 11 and ½ hour, and a second minor fatigue detection 708 occurs at the 19$^{th}$ hour. An audible alarm may be triggered when a minor fatigue level is detected, alerting the user to take a break soon. An extreme fatigue detection 710 occurs just prior to the 24-hour mark on the timeline 702. When an extreme fatigue level is detected, the proprietary application may immediately audibly notify the user to safely find a place to rest. The frequency, time of day, and other conditions associated with the detections 706, 708, and 710 may be stored within the proprietary application, on the employee management system, and/or on the proprietary application's remote admin system.

Figure 8:
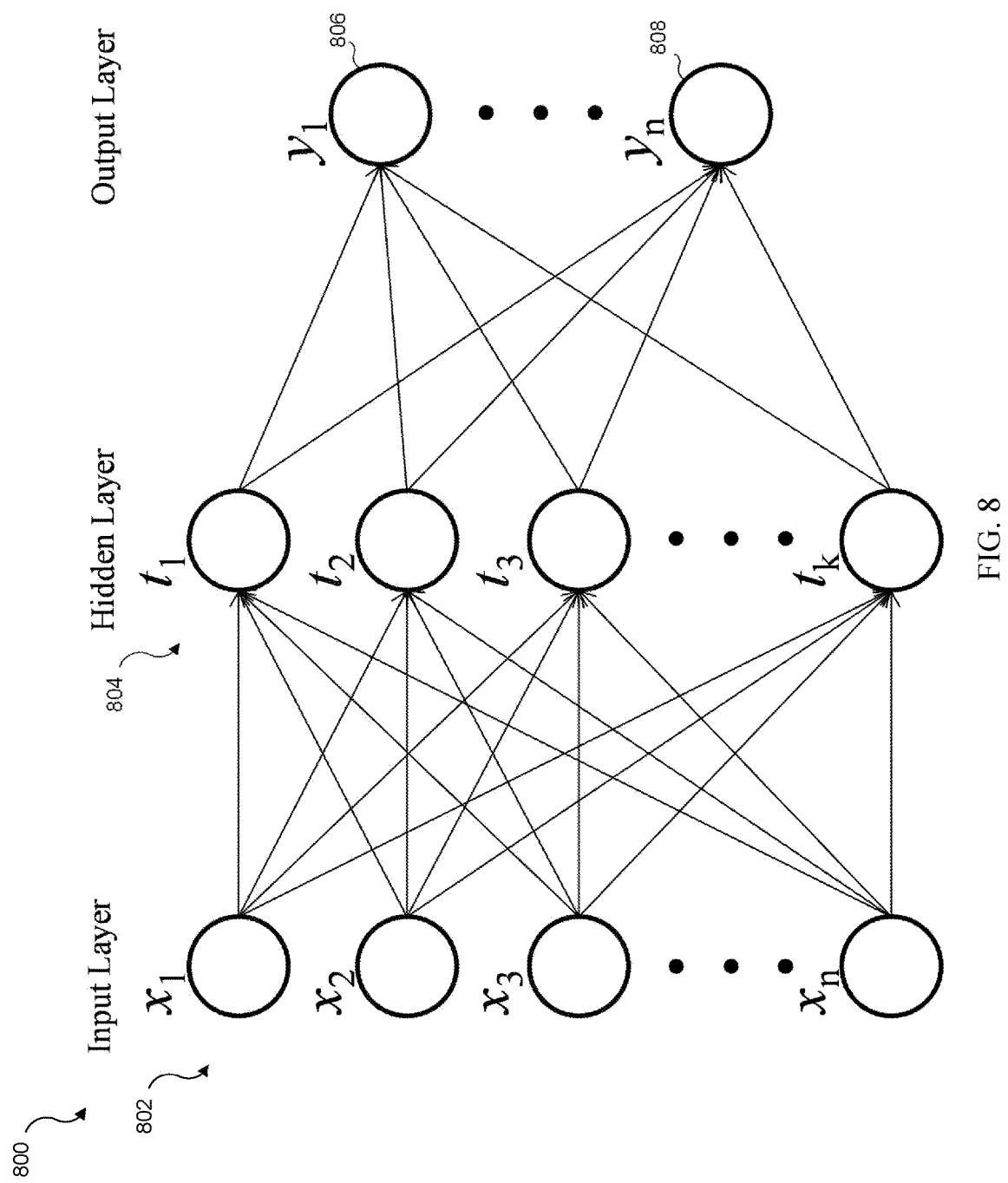
FIG. 8 illustrates a diagrammatic view of one embodiment of a neural network.

Referring now to FIG. 8, there is illustrated a diagrammatic view of one embodiment of a neural network 800. Neural networks are non-parametric methods used for machine learning such as pattern recognition and optimization. They are able to generate an output based on a weighted sum of inputs, which is passed through an activation function. Typically, the activation function determines the output by summing the inputs multiplied by the weights. A basic activation function is that of $y=f(\Sigma wx)$, where x is the vector of inputs, w is the vector of weights, $f(.)$ is the activation function, and y is the output vector. It will be understood by those skilled in the art that variations on the activation function may be used or represented in other ways, such as the activation function: $\alpha=\Sigma_{i=0}^{i=n} W_i X_i$. Other activation functions that may be used include the softmax activation function, which is generally used for probabilities:

$$(x) = \frac{e^x}{\Sigma e^x},$$

or a tanh sigmoid function: $\tanh(x)=2\sigma(2x)-1$.

The inputs, weights, and outputs may be organized within a multilayer perceptron (MLP), wherein there is an input layer, one or more hidden layers, and an output layer. As shown in the network 800, a plurality of inputs 802 reside in the input layer, a plurality of neurons 804 (the weights) reside in the hidden layer or layers, and at least one output 806 up to an nth output 808 reside in the output layer. It will be appreciated that the neural network 800 may contain any number of inputs, neurons, or outputs from 1 to n. Thus, this creates a feedforward network. A feedforward network, as shown in FIG. 8, is called such because the inputs in the input layer feed into each of the neurons in the hidden layer or layers, which in turn feed into each of the outputs in the output layer, with each output in the output layer providing a result. When used with the biometric tracking and user condition prediction software disclosed herein, the outputs may indicate results obtained for a particular condition. For example, if blink rate is being tracked to predict the drowsiness of a user, the inputs may be multiple blink rates tracked in real time that are fed into the neural network, multiplied by the weights, and passed through the activation function to achieve one or more outputs.

Although there could be any number of hidden layers, typically ranging from one to three, it will be appreciated by those skilled in the art that a single hidden layer can estimate differentiable functions, provided there are enough hidden units. A higher number of hidden layers also increases processing time and the amount of adjustments needed during neural network training. One method of determining the number of needed neurons in the hidden layer is represented by: $N_h = \sqrt{N_i \cdot N_o}$, where $N_h$ is the number of hidden nodes, $N_i$ is the number of input nodes, and $N_o$ is the number of output nodes. It will be appreciated that the number of neurons will change depending on the number of inputs and outputs. Further, the method for determining the number of neurons may also be different, as this is but one example.

It will be understood by those skilled in the art that the neural network would be trained in order for the neural network to become more accurate. Various training methods exist, such as supervised learning where random weights are fed into the neural network and adjusted accordingly, back-propagation methods, or other methods. Activation functions are applied to the weighted sum of the inputs to generate a certain outcome. The weights may be set to small random values initially. The input pattern may then be applied and propagated through the network until a certain output is generated for the hidden layer. One other training method may be to feed inputs into the neural network that are expected to indicate a fatigued or hazardous state for a user as well as awake states, to initially train the neural network on those values, and then validate the weights generated from the neural network by another set of data, and predict fatigued or hazardous user conditions and test the accuracy of such predictions. Training results may be collected including the number of true positives, true negatives, false positives, and false negatives. If the number or percentage of false positives and negatives appear too high, additional training may be required. After initial training, the neural network would then be trained for each particular user, to synchronize the neural network with each user.

The outputs of the hidden layer are used as entries for the output layer. Weighted and summed up, they are passed through an activation function to produce the final output. The way the weights are modified to meet the desired results defines the training algorithm and is essentially an optimization problem. When the activation functions are differentiable, the error back-propagation algorithm may be a good approach in progressing towards the minimum of the error function. The errors are then passed back through the network using the gradient, by calculating the contribution of each hidden node and deriving the adjustments needed to generate an output that is closer to the target value. Weights can then be adjusted taking also into account the modification from the previous cycle, this method being called back-propagation with momentum rate.

Figure 9:
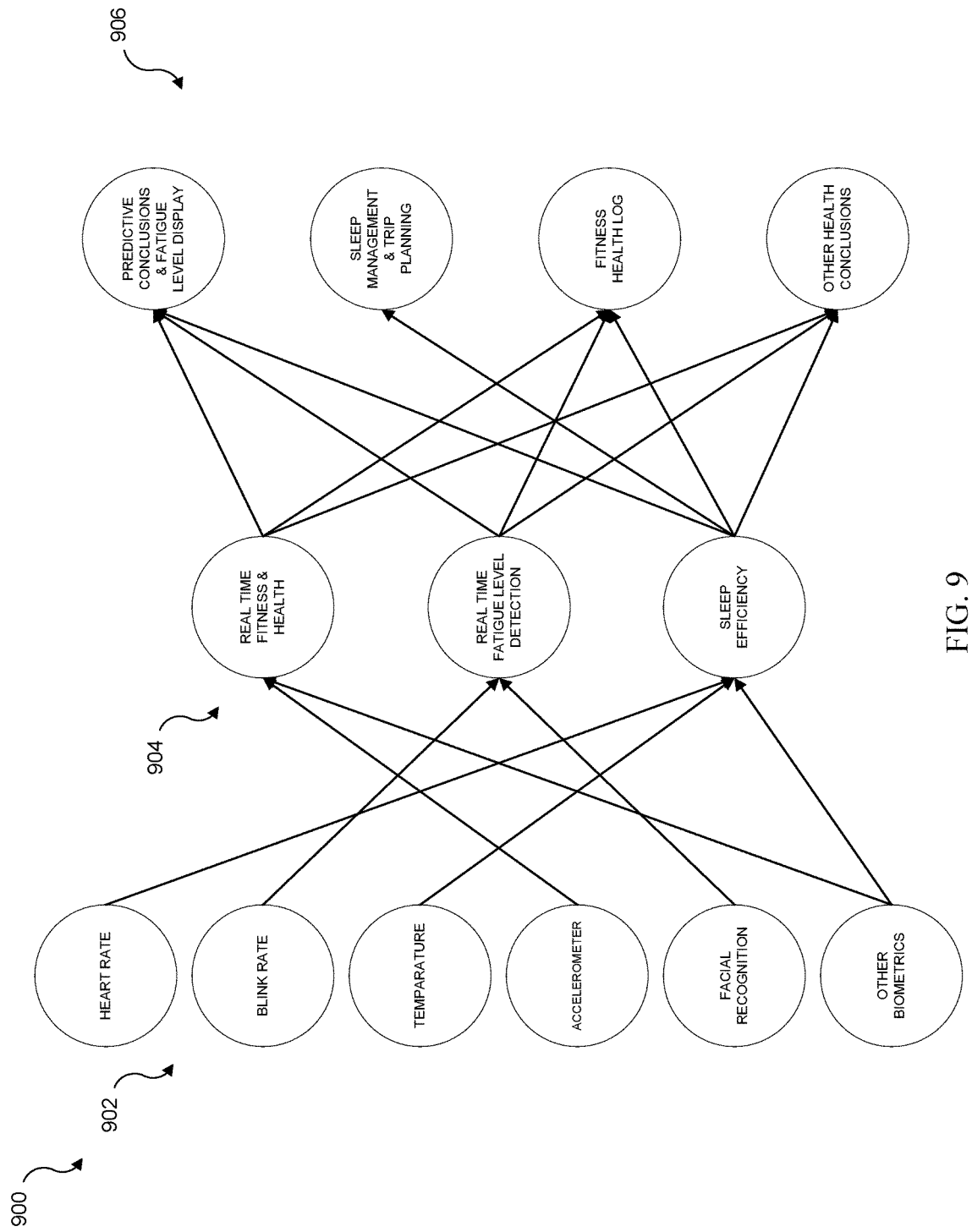
FIG. 9 illustrates a diagrammatic view of a multiple neural network user condition tracking and prediction system.

Referring now to FIG. 9, there is illustrated a diagrammatic view of a multiple neural network user condition tracking and prediction system 900. It will be understood by those skilled in the art that neural networks can be set up and trained in various ways. It will be appreciated that the neural network may be organized to allow for the functionality disclosed herein. It will also be understood that a different neural network may be used for each type of condition being predicted for the user. For example, one neural network may estimate wide awake hours based on the amount of user REM sleep, one network may predict when a user is nodding off based on blink rate and head movement inputs, one network may evaluate user sleep efficiency based on heart rate, temperature and body movement, etc.

FIG. 9 shows a plurality of inputs 902 that may be the various tracked user biometrics, such as heart rate, blink rate, temperature, accelerometer data, facial recognition, and other biometrics. To process the gathered biometrics and to estimate or predict user conditions or behaviors, certain inputs may be passed into certain neural networks, with each neural network being one of a plurality of neural networks 904. Each neural network of the plurality of neural networks 904 may be trained to predict particular user conditions, such as real time fitness and health such as the overall health of the user taken from accelerometer and other biometric data inputs, real time fatigue level detection taken from blink rate and facial recognition biometric data, sleep efficiency taken from heart rate, temperature, and other biometric data, and other neural network types.

Figure 10:
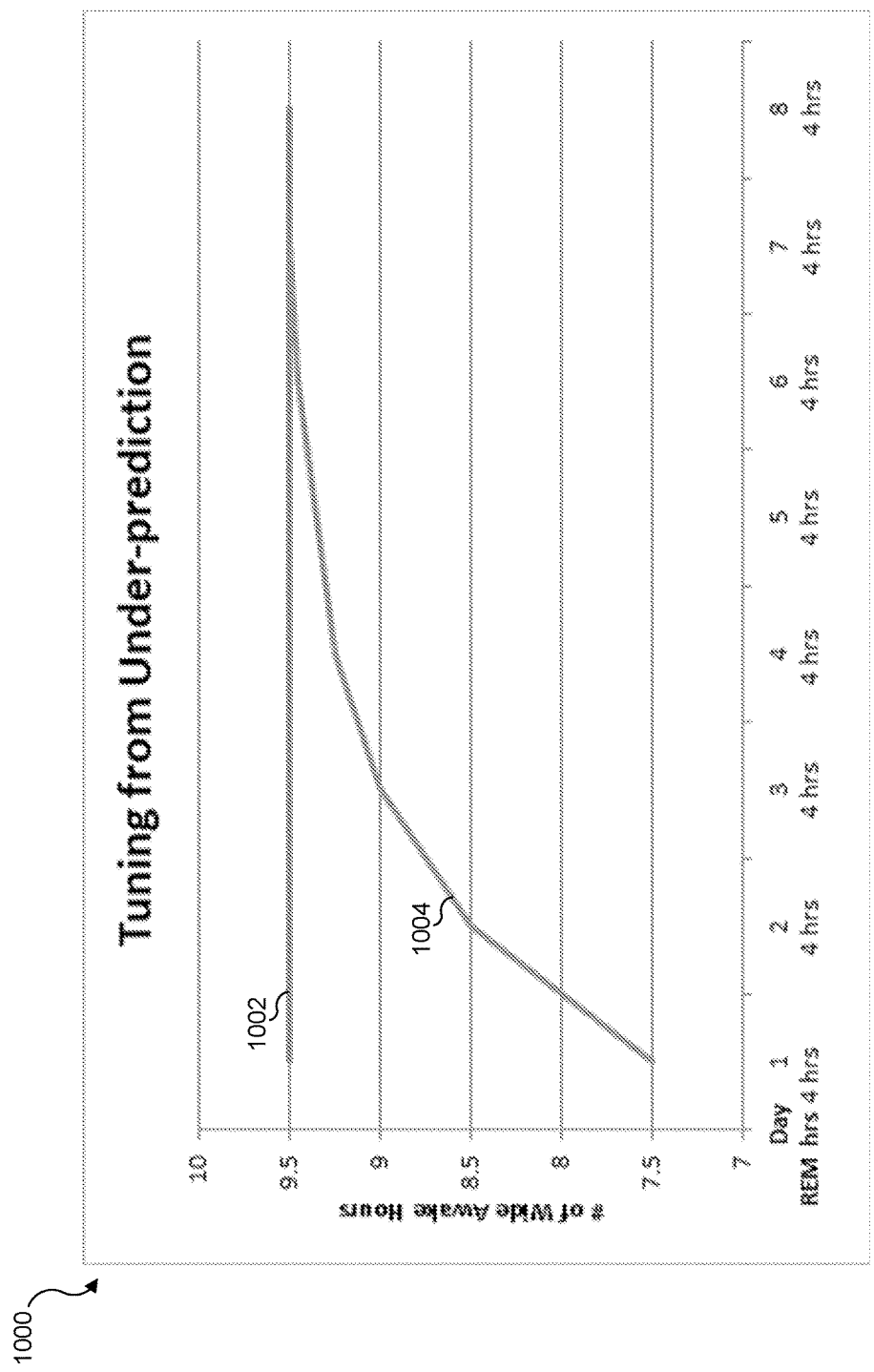
FIG. 10 illustrates one embodiment of an under-prediction tuning chart.
Figure 11:
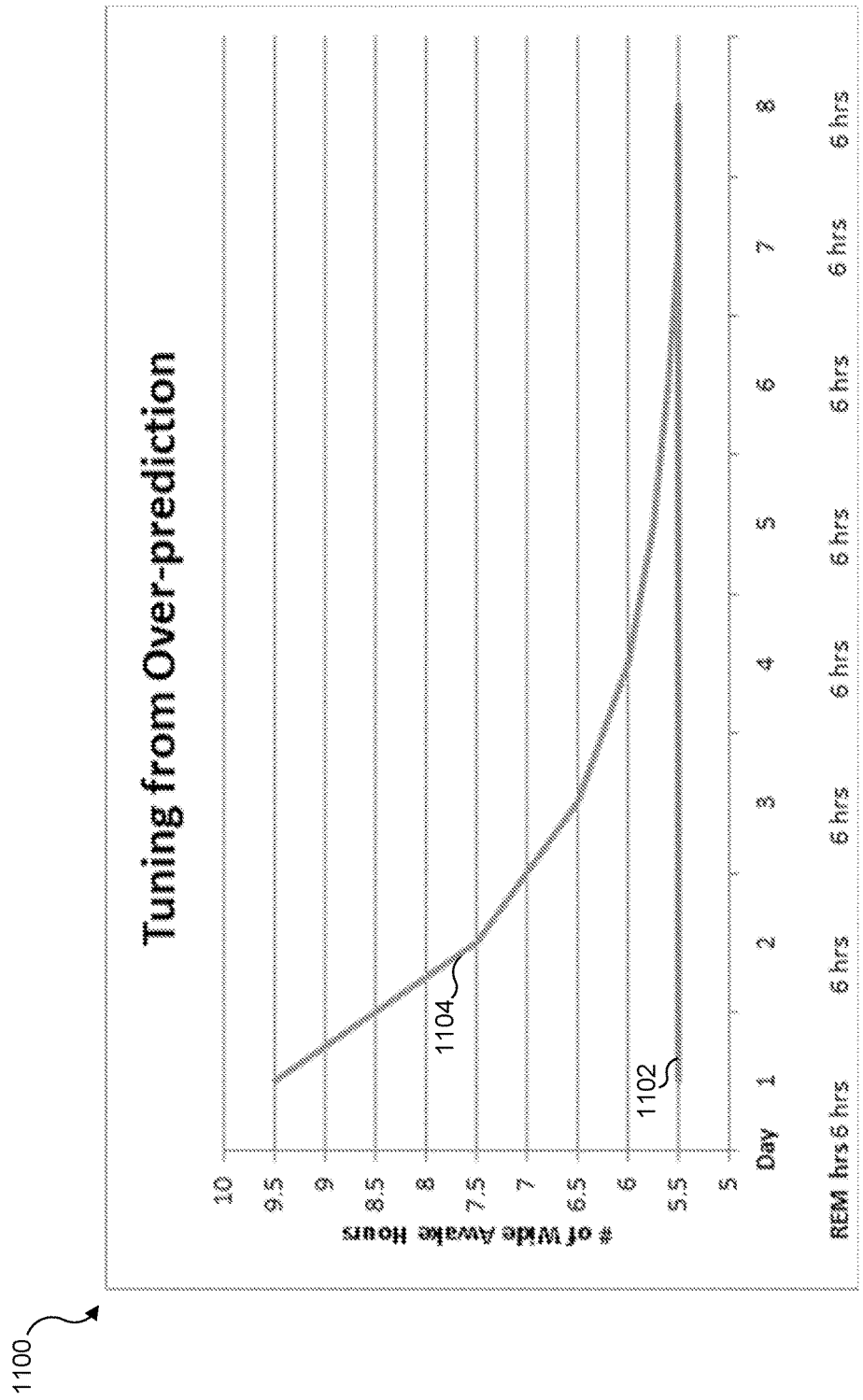
FIG. 11 illustrates one embodiment of an over-prediction tuning chart.
Figure 12:
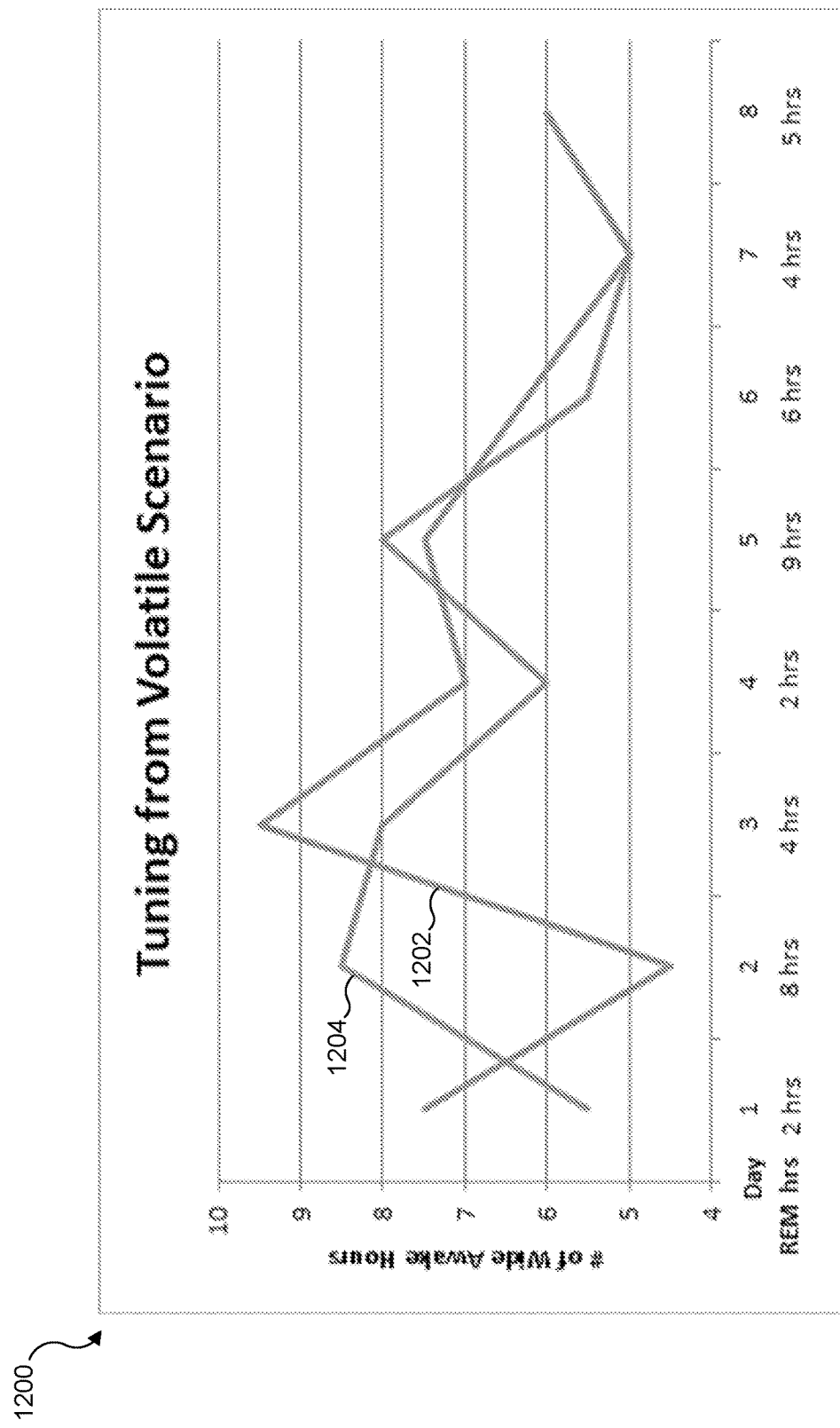
FIG. 12 illustrates one embodiment of a volatile scenario tuning chart.

As examples of the application of the systems and methods described herein, the below Tables, and FIGS. 10, 11, and 12, provide various biometric thresholds, tuning scenarios, and potential biometrics for tracking for a driver management system. It will be understood that these principles may be applied to other industries as well. These neural networks may then provide outputs that fall within a plurality of user conditions reporting paradigms 906. For instance, the real time fitness and health and real time fatigue level detection neural networks may provide outputs for use in predictive conclusions & fatigue level displays, a fitness health log, and other health conclusions. The sleep efficiency neural network may provide outputs for use in predictive conclusions and fatigue level displays, sleep management and trip planning, a fitness health log, and other health conclusions. It will be understood that each of the plurality of neural networks 904, while each are shown as a single entity in FIG. 9, may be large neural networks having multiple input layers, hidden layers, output layers, and multiple inputs, neurons, and/or outputs for weighting and activating data, but may also be smaller neural networks such as having even a single neuron if such is feasible to produce the desired outputs.

A fatigue alert triggering event may occur when more than one biometric has surpassed the normal threshold, or when one biometric measurement far exceeds, or frequently exceeds, the normal threshold. Table 1 lists various biometrics and their associated normal states and common outliers.

TABLE 1

| Biometrics | Normal | Outlier |
| --- | --- | --- |
| Blink rate | 17-26 blinks/minute | 28% increase |
| Blink duration | 0.2-0.3 seconds | 1-2 seconds |
| Head tilt | 0 nods/minute | 3-6 nods/minute |
| Body temp | 98.6 degrees F. | ±3 degrees F. |
| Heart rate | 60-100 beats/minute | <60 or >104 beats/minute |
| Yawn rate | 0-1 yawn/minute | >1 yawn/minute |
| REM sleep time | 5-7 hours | 1-4 hours |
| Mental lapse through pupil location | No iris flutters | 0.5 seconds before eye closure |
| Focus point through pupil location | Looking away for 0.5-1.5 seconds | Looking away for >2 seconds |

In an average scenario, the required amount of sleep for every driver is 8 hours, which equates to about 7 hours of REM sleep. When the driver wakes up, the proprietary application displays the exact time the driver is expected to feel fatigued, typically around the 8$^{th}$ hour of driving. When a driver first begins using the application, the conclusions are based on industry averages but will become more accurate based on the application's learned habits of the driver. Around the 8$^{th}$ hour of driving, the application may detect that the driver's blink rate has increased by 28%. The application may then audibly warn the driver that the driver is feeling slightly fatigued and suggest that the driver take a short break. At the 10$^{th}$ hour of driving, the application may detect eye flutters before the driver blinks, in addition to a high blink rate. The application may then audibly notify the driver that the driver should get some sleep. At this time, multiple fatigue sensors may be detecting outlying fatigue levels further indicating that the driver is in an extreme fatigued state.

In atypical scenarios, the conditions may differ. For example, some drivers may function on less sleep than the typical 8 hours, or simply may not get a full 8 hour rest due to various circumstances. For example, if a driver were to only get 4 hours of REM sleep, when the driver awakes, the application may display that the driver can expect to feel fatigued around the 5$^{th}$ hour of driving. Around the 4$^{th}$ hour of driving, the application may detect increased fatigue, such as detecting three yawns per minute. The application then may audibly alert the driver that the driver is slightly fatigued and suggest a short break. Just before the sixth hour of driving, the application may then detect a 28% increased blink rate, eye flutters, and three distinct head nods in one minute. The application may then audibly alert the driver that the driver is highly fatigued and needs to get some sleep.

After two weeks, the application should be well integrated into the driver's habits and biometric trends. Instead of using industry averages for the conclusions, the individual averages may be used instead. The application will then display customized conclusions for each individual driver. Some drivers may be able to work a full 8-hour day even with only three hours of REM sleep. The driver may not fall into the categories of what is considered normal, but because of the learned trends, recorded individual averages, and multiple biometric sensors, the fatigue level can still accurately be predicted and displayed on an individual basis.

As another example, while a normal driver may get 8 hours of sleep each night, the application knows that a particular driver only gets 3 hours of REM sleep each night. The application has also previously recorded this driver as being fully awake for 8 hours each day, and predicts he will feel fatigued around the 8th hour of driving.

Around the 8th hour of driving, application detects his blink rate has increased by 15% and a 1 second blink duration. Based on this particular driver's previously recorded biometric averages, his blink rate only increases by 15% at most. The application audibly notifies the driver to take a short break because he is slightly fatigued.

Around the 9.5th hour of driving, the application detects 5 head nods in one minute. Based on previously recorded averages, this particular driver nods more often than the industry average, therefore setting a higher outlier for himself. The application is also detecting high blink rate and long blink duration. The driver is then audibly notified that he is highly fatigued and needs to get some sleep soon.

The application will be reassured unsupervised learning. The software will be programed with numerous examples using the industry averages such as those shown in Table 1 as the initial reference points and thresholds. As drivers continue to use the application, the biometric data collected will allow the program to learn each driver's daily fatigue patterns and display more accurate conclusions and notifications on an individual basis.

When a driver first uses the system, it is typically best to start it before they go to sleep while wearing a sleep-monitoring device such as a wristband that can detect heart rate. The application will determine how much REM sleep the driver got, and be able to display the time of day the driver can expect to start feeling fatigued. The very first prediction may not be the most accurate because it has not yet learned the driver's daily fatigue patterns. If the driver got 5-7 hours of REM sleep, the application will first display to him/her that he/she can expect to feel fatigued 8 hours after waking up. When the driver gets behind the wheel, before he/she starts driving, he/she will equip a facial recognition device such as a smart Bluetooth headset. As the driver is driving, the application will continually collect and store biometric data from multiple wearables containing a variety of sensors; in this case a smart watch and a smart Bluetooth headset. If this very first prediction is over estimated, the sensors from the smart Bluetooth headset will still be able to stop the driver from falling asleep at the wheel. If around the 4th hour after waking the headset detects multiple head nods in one minute and a 28% increase in blink rate, it will automatically audibly alarm the driver, and the application will notify the fleet manager. The next day, if the driver gets the same amount of sleep, the application will display that he/she can expect to feel fatigued around the 6th hour after waking [(8+4)/2]. The application will remember the times of day the driver felt fatigued (determined by facial sensors), and the times and quality of sleep (determined by sleep sensors). This new incoming data will be averaged together to accurately determine when the driver can expect to feel fatigued.

After the driver uses the application for the learning period, the industry averages that were used when the app was first turned on will no longer be used in the calculation of fatigue levels; only the averages obtained from the individual driver will be used. The application will be highly accurate at this point because it has learned the driver's daily fatigue patterns and only uses the respective individual averages. Even after the learning period, the application will continue to monitor and record the sensors in order to store more individual averages for the predictive conclusion calculation.

A consistent scenario is detailed in Table 2.

TABLE 2

| | Consistent Scenario | | |
|---|---|---|---|
| Day | Sensor Inputs for Calculation | App Predictions | Driver Results Detected |
| 1 | 6 REM hours (11pm-5am) | Slightly fatigued 2pm, Heavily fatigued 5pm | Slightly fatigued 2pm, Heavily fatigued 5pm |
| 2 | 6 REM hours (11pm-5am), 6 REM hours & 16 awake hours (day 1) | Slightly fatigued 2pm, Heavily fatigued 5pm | Slightly fatigued 2pm, Heavily fatigued 5pm |
| 3 | 6 REM hours (11pm-5am), 6 REM hours & 16 awake hours (day 1), 6 REM hours & 16 awake hours (day 2) | Slightly fatigued 2pm, Heavily fatigued 5pm | Slightly fatigued 2pm, Heavily fatigued 5pm |

TABLE 2-continued

Consistent Scenario

| Day | Sensor Inputs for Calculation | App Predictions | Driver Results Detected |
|---|---|---|---|
| 4 | 6 REM hours (11pm-5am), 6 REM hours & 16 awake hours (day 1), 6 REM hours & 16 awake hours (day 2), 6 REM hours & 16 awake hours (day 3) | Slightly fatigued 2pm, Heavily fatigued 5pm | Slightly fatigued 2pm, Heavily fatigued 5pm |
| 5 | 6 REM hours (11pm-5am), 6 REM hours & 16 awake hours (day 1), 6 REM hours & 16 awake hours (day 2), 6 REM hours & 16 awake hours (day 3), 6 REM hours & 16 awake hours (day 4) | Slightly fatigued 2pm, Heavily fatigued 5pm | Slightly fatigued 2pm, Heavily fatigued 5pm |
| 6 | 6 REM hours (11pm-5am), 6 REM hours & 16 awake hours (day 1), 6 REM hours & 16 awake hours (day 2), 6 REM hours & 16 awake hours (day 3), 6 REM hours & 16 awake hours (day 4), 6 REM hours & 16 awake hours (day 5) | Slightly fatigued 2 pm, Heavily fatigued 5 pm | Slightly fatigued 2pm, Heavily fatigued 5pm |
| 7 | 6 REM hours (11pm-5am), 6 REM hours & 16 awake hours (day 1), 6 REM hours & 16 awake hours (day 2), 6 REM hours & 16 awake hours (day 3), 6 REM hours & 16 awake hours (day 4), 6 REM hours & 16 awake hours (day 5), 6 REM hours & 16 awake hours (day 6) | Slightly fatigued 2pm, Heavily fatigued 5pm | Slightly fatigued 2pm, Heavily fatigued 5pm |
| 8 | 6 REM hours (11pm-5am), 6 REM hours & 16 awake hours (day 1), 6 REM hours & 16 awake hours (day 2), 6 REM hours & 16 awake hours (day 3), 6 REM hours & 16 awake hours (day 4), 6 REM hours & 16 awake hours (day 5), 6 REM hours & 16 awake hours (day 6), 6 REM hours & 16 awake hours (day 7) | Slightly fatigued 2pm, Heavily fatigued 5pm | Slightly fatigued 2pm, Heavily fatigued 5pm |

Referring now to FIG. 10, there is illustrated one embodiment of an under-prediction tuning chart 1000. An under-predicted start scenario example is detailed in Table 3.

TABLE 3

Under-Predicted Start Scenario

| Day | Sensor Inputs for Calculation | App Predictions | Driver Results Detected |
|---|---|---|---|
| 1 | 4 REM hours (1am-5am) | Slightly fatigued 12pm, Heavily fatigued 3pm | Slightly fatigued 2pm, Heavily fatigued 5pm |
| 2 | 4 REM hours (1am-5am), 4 REM hours & 18 awake hours (day 1) | Slightly fatigued 1pm, Heavily fatigued 4pm | Slightly fatigued 2pm, Heavily fatigued 5pm |
| 3 | 4 REM hours (1am-5am), 4 REM hours & 18 awake hours (day 1), 4 REM hours & 18 awake hours (day 2) | Slightly fatigued 1:30pm, Heavily fatigued 4:30pm | Slightly fatigued 2pm, Heavily fatigued 5pm |
| 4 | 4 REM hours (1am-5am), 4 REM hours & 18 awake hours (day 1), 4 REM hours & 18 awake hours (day 2), 4 REM hours & 18 awake hours (day 3) | Slightly fatigued 1:45pm, Heavily fatigued 4:45pm | Slightly fatigued 2pm, Heavily fatigued 5pm |
| 5 | 4 REM hours (1am-5am), 4 REM hours & 18 awake hours (day 1), 4 REM hours & 18 awake hours (day 2), 4 REM hours & 18 awake hours (day 3), 4 REM hours & 18 awake hours (day 4) | Slightly fatigued 1:50pm, Heavily fatigued 4:50pm | Slightly fatigued 2pm, Heavily fatigued 5pm |
| 6 | 4 REM hours (1am-5am), 4 REM hours & 18 awake hours (day 1), 4 REM hours & 18 awake hours (day 2), 4 REM hours & 18 awake hours (day 3), 4 REM hours & 18 awake hours (day 4), 4 REM hours & 18 awake hours (day 5) | Slightly fatigued 1:55pm, Heavily fatigued 4:55pm | Slightly fatigued 2pm, Heavily fatigued 5pm |
| 7 | 4 REM hours (1am-5am), 4 REM hours & 18 awake hours (day 1), 4 REM hours & 18 awake hours (day 2), 4 REM hours & 18 awake hours (day 3), 4 REM hours & 18 awake hours (day 4), 4 REM hours & 18 awake hours (day 5), 4 REM hours & 18 awake hours (day 6) | Slightly fatigued 2pm, Heavily fatigued 5pm | Slightly fatigued 2pm, Heavily fatigued 5pm |

TABLE 3-continued

Under-Predicted Start Scenario

| Day | Sensor Inputs for Calculation | App Predictions | Driver Results Detected |
|---|---|---|---|
| 8 | 4 REM hours (1am-5am), 4 REM hours & 18 awake hours (day 1), 4 REM hours & 18 awake hours (day 2), 4 REM hours & 18 awake hours (day 3), 4 REM hours & 18 awake hours (day 4), 4 REM hours & 18 awake hours (day 5), 4 REM hours & 18 awake hours (day 6), 4 REM hours & 18 awake hours (day 7) | Slightly fatigued 2pm, Heavily fatigued 5pm | Slightly fatigued 2pm, Heavily fatigued 5pm |

The chart 1000 shows a first line 1002 representing a driver's actual behavior while a second line 1004 represents predicted behavior, predicted by the predictive/analytic engine 104. The x-axis of the chart 1000 shows that the driver is receiving four hours or REM sleep every day over an eight day period. The y-axis shows the number of wide awake hours for each day. The first line 1002 remains constant at 9.5 wide awake hours for each of the eight days. Thus, even though the driver is only getting four hours of REM sleep each night, the driver is able to remain wide awake for 9.5 hours each day. This is atypical behavior. The predictive engine will generally initially predict a lower number of wide awake hours for a driver who only gets four hours of REM sleep. The chart 1000 demonstrates this by showing the second line 1004 starting at 7.5 wide awake hours, as the predictive engine predicts that a driver will only have 7.5 wide awake hours with only four hours of REM sleep. However, as the application continues to monitor the driver's behavior and biometrics, the application will begin to adjust the predictions accordingly, gradually moving the predicted number of wide awake hours up each day as the driver continues to remain wide awake for 9.5 hours each day. By the seventh day, the second line 1004 reaches 9.5 hours, syncing with the driver's behavior. If the driver begins a different pattern of behavior, the application may then alter its predictions in a similar manner as shown in the chart 1000 or as otherwise described herein.

Referring now to FIG. 11, there is illustrated one embodiment of an over-prediction tuning chart 1100. An over-predicted start scenario example is detailed in Table 4.

TABLE 4

Over-Predicted Start with Naps Scenario

| Day | Sensor Inputs for Calculation | App Predictions | Driver Results Detected |
|---|---|---|---|
| 1 | 6 REM hours (11pm-5am) | Slightly fatigued 2pm, Heavily fatigued 5pm | Slightly fatigued 10am, Heavily fatigued 1pm, 1 REM hour nap (2pm), Slightly fatigued 6pm |
| 2 | 6 REM hours (11pm-5am), 7 REM hours & 15 awake hours (day 1) | Slightly fatigued at 12pm, Heavily fatigued 3pm | Slightly fatigued 10am, Heavily fatigued 1pm, 1 REM hour nap (2pm), Slightly fatigued 6pm |
| 3 | 6 REM hours (11pm-5am), 7 REM hours & 15 awake hours (day 1), 7 REM hours & 15 awake hours (day 2) | Slightly fatigued 11am, Heavily fatigued 2pm | Slightly fatigued 10am, Heavily fatigued 1pm, 1 REM hour nap (2pm), Slightly fatigued 6pm |
| 4 | 6 REM hours (11pm-5am), 7 REM hours & 15 awake hours (day 1), 7 REM hours & 15 awake hours (day 2), 7 REM hours & 15 awake hours (day 3) | Slightly fatigued 10:30am, Heavily fatigued 1:30pm | Slightly fatigued 10am, Heavily fatigued 1pm, 1 REM hour nap (2pm), Slightly fatigued 6pm |
| 5 | 6 REM hours (11pm-5am), 7 REM hours & 15 awake hours (day 1), 7 REM hours & 15 awake hours (day 2), 7 REM hours & 15 awake hours (day 3), 7 REM hours & 15 awake hours (day 4) | Slightly fatigued 10:15am, Heavily fatigued 1:15pm | Slightly fatigued 10am, Heavily fatigued 1pm, 1 REM hour nap (2pm), Slightly fatigued 6pm |
| 6 | 6 REM hours (11pm-5am), 7 REM hours & 15 awake hours (day 1), 7 REM hours & 15 awake hours (day 2), 7 REM hours & 15 awake hours (day 3), 7 REM hours & 15 awake hours (day 4), 7 REM hours & 15 awake hours (day 5) | Slightly fatigued 10:05am, Heavily fatigued 1:05pm | Slightly fatigued 10am, Heavily fatigued 1pm, 1 REM hour nap (2pm), Slightly fatigued 6pm |
| 7 | 6 REM hours (11pm-5am), 7 REM hours & 15 awake hours (day 1), 7 REM hours & 15 awake hours (day 2), 7 REM hours & 15 awake hours (day 3), 7 REM hours & 15 awake hours (day 4), 7 REM hours & 15 awake hours (day 5), 7 REM hours & 15 awake hours (day 6) | Slightly fatigued 10am, Heavily fatigued 1pm | Slightly fatigued 10am, Heavily fatigued 1pm, 1 REM hour nap (2pm), Slightly fatigued 6pm |

TABLE 4-continued

Over-Predicted Start with Naps Scenario

| Day | Sensor Inputs for Calculation | App Predictions | Driver Results Detected |
|---|---|---|---|
| 8 | 6 REM hours (11pm-5am),<br>7 REM hours & 15 awake hours (day 1),<br>7 REM hours & 15 awake hours (day 2),<br>7 REM hours & 15 awake hours (day 3),<br>7 REM hours & 15 awake hours (day 4),<br>7 REM hours & 15 awake hours (day 5),<br>7 REM hours & 15 awake hours (day 6),<br>7 REM hours & 15 awake hours (day 7) | Slightly fatigued 10am,<br>Heavily fatigued 1pm | Slightly fatigued 10am,<br>Heavily fatigued 1pm |

The chart 1100 shows a first line 1102 representing a driver's actual behavior while a second line 1104 represents predicted behavior, predicted by the predictive/analytic engine 104. The x-axis of the chart 1100 shows that the driver is receiving six hours or REM sleep every day over an eight day period. The y-axis shows the number of wide awake hours. The first line 1102 remains constant at 5.5 wide awake hours for each of the eight days. In this example, the predictive engine has predicted that the driver will be able to maintain 9.5 wide awake hours with six hours of REM sleep, either based on a starting point for the predictive engine with no data yet received from the driver, or due to the driver's past behavior, which has now changed. However, as the application continues to monitor the driver's behavior and biometrics, the application will begin to adjust the predictions accordingly, gradually moving the predicted number of wide awake hours down each day as the driver continues to remain wide awake for only 5.5 hours each day. By the seventh day, the second line 1104 reaches 5.5 hours, syncing with the driver's behavior. If the driver begins a different pattern of behavior, the application may then alter its predictions in a similar manner as shown in the chart 1100 or as otherwise described herein.

Referring now to FIG. 12, there is illustrated one embodiment of a volatile scenario tuning chart 1200. A volatile scenario is detailed in Table 5.

TABLE 5

Volatile Scenario

| Day | Sensor Inputs for Calculation | App Predictions | Driver Results Detected |
|---|---|---|---|
| 1 | 2 REM hours (3am-5am) | Slightly fatigued 10am,<br>Heavily fatigued 1pm | Slightly fatigued 12pm,<br>Heavily fatigued 3pm,<br>1 REM hour nap (4pm),<br>Slightly fatigued 7pm,<br>Heavily fatigued 9pm |
| 2 | 8 REM hours (11pm-7am),<br>3 REM hours & 19 awake hours (day 1) | Slightly fatigued 3:30pm,<br>Heavily fatigued 5:30pm | Slightly fatigued at 12pm,<br>Heavily fatigued 1pm,<br>1 REM hour nap (2pm),<br>Slightly fatigued 7pm,<br>heavily fatigued 10pm |
| 3 | 4 REM hours (12am-4am),<br>3 REM hours & 19 awake hours (day 1),<br>9 REM hours & 13 awake hours (day 2) | Slightly fatigued 11:30am,<br>Heavily fatigued 1:45pm | Slightly fatigued 9am,<br>Heavily fatigued 10am,<br>1 REM hour nap (11am),<br>Slightly fatigued 4pm,<br>Heavily fatigued 7pm |
| 4 | 2 REM hours (12am-2am),<br>3 REM hours & 19 awake hours (day 1),<br>9 REM hours & 13 awake hours (day 2),<br>5 REM hours & 17 awake hours (day 3) | Slightly fatigued 8am,<br>Heavily fatigued 10am | Slightly fatigued 9am,<br>Heavily fatigued 11am,<br>1 REM hour nap (12pm),<br>Slightly fatigued 4pm,<br>Heavily fatigued 5pm |
| 5 | 9 REM hours (12am-9am),<br>3 REM hours & 19 awake hours (day 1),<br>9 REM hours & 13 awake hours (day 2),<br>5 REM hours & 17 awake hours (day 3),<br>3 REM hours & 19 awake hours (day 4) | Slightly fatigued 5pm,<br>Heavily fatigued 7pm | Slightly fatigued 4:30pm,<br>Heavily fatigued 6:30pm,<br>1 REM hour nap (7:30pm),<br>Slightly fatigued 12am,<br>Heavily fatigued 3am |
| 6 | 6 REM hours (4am-10am),<br>3 REM hours & 19 awake hours (day 1),<br>9 REM hours & 13 awake hours (day 2),<br>5 REM hours & 17 awake hours (day 3),<br>3 REM hours & 19 awake hours (day 4),<br>10 REM hours & 12 awake hours (day 5) | Slightly fatigued 3pm,<br>Heavily fatigued 6pm | Slightly fatigued 3:15pm,<br>Heavily fatigued 6:15pm,<br>1 REM hour nap (7:15pm),<br>Slightly fatigued 12am,<br>Heavily fatigued 2am |
| 7 | 4 REM hours (3am-7am),<br>3 REM hours & 19 awake hours (day 1),<br>9 REM hours & 13 awake hours (day 2),<br>5 REM hours & 17 awake hours (day 3),<br>3 REM hours & 19 awake hours (day 4),<br>10 REM hours & 12 awake hours (day 5),<br>7 REM hours & 13 awake hours (day 6) | Slightly fatigued 12pm,<br>Heavily fatigued 2pm | Slightly fatigued 12pm,<br>Heavily fatigued 2pm,<br>1 REM hour nap (3pm),<br>Slightly fatigued 9pm,<br>Heavily fatigued 12am |

TABLE 5-continued

Volatile Scenario

| Day | Sensor Inputs for Calculation | App Predictions | Driver Results Detected |
|---|---|---|---|
| 8 | 5 REM hours (3am-8am), 3 REM hours & 19 awake hours (day 1), 9 REM hours & 13 awake hours (day 2), 5 REM hours & 17 awake hours (day 3), 3 REM hours & 19 awake hours (day 4), 10 REM hours & 12 awake hours (day 5), 7 REM hours & 13 awake hours (day 6), 5 REM hours & 17 awake hours (day 7) | Slightly fatigued 2:30pm, Heavily fatigued 4:30pm | Slightly fatigued 2:30pm, Heavily fatigued 4:30pm |

The chart 1200 shows a first line 1202 representing a driver's actual behavior while a second line 1204 represents predicted behavior, predicted by the predictive/analytic engine 104. The x-axis of the chart 1200 shows that the driver is receiving a variable amount of hours of REM sleep each day over an eight day period. The y-axis shows the number of wide awake hours for each of those days. On day 1, the driver receives only two hours of REM sleep, and is wide awake for about 5.5 hours that day, while the application predicts the driver will have 7.5 wide awake hours, either due to an initial default or due to past learned driver behavior. On the second day, the driver receives 8 hours of REM sleep, but only remains wide awake for about 4.5 hours that day. The application attempts to adjust the prediction based on the day 1 occurrence of low REM sleep, but high wide awake hours, but over-predicts for day 2 by predicting the driver will be wide awake for about 8.5 hours when the driver actually is only wide awake for about 4.5 hours. On day 3, the driver gets 4 hours of REM sleep and is wide awake for 9.5 hours. The application's prediction is closer for day 3, as it predicts 8 wide awake hours. On day 4, the driver gets only 2 hours of REM sleep and stays awake for 7 hours. The application gets closer still to the driver's actual behavior by predicting 6 wide awake hours. On day 5, the driver gets 9 hours of REM sleep and is wide awake for 8 hours, while the application predicts about 7.5 wide awake hours. On day 6, the driver gets 6 hours of REM sleep and is wide awake for about 6 hours, while the application predicts about 5.5 hours of wide awake hours. On day seven, the application syncs with the driver, predicting that the driver will be wide awake for 5 hours with 4 hours of REM sleep, which is in line with the driver's actual behavior for day 7. This synchronization continues into day 8 with 5 hours of REM sleep and 6 wide awake hours.

Figure 13:
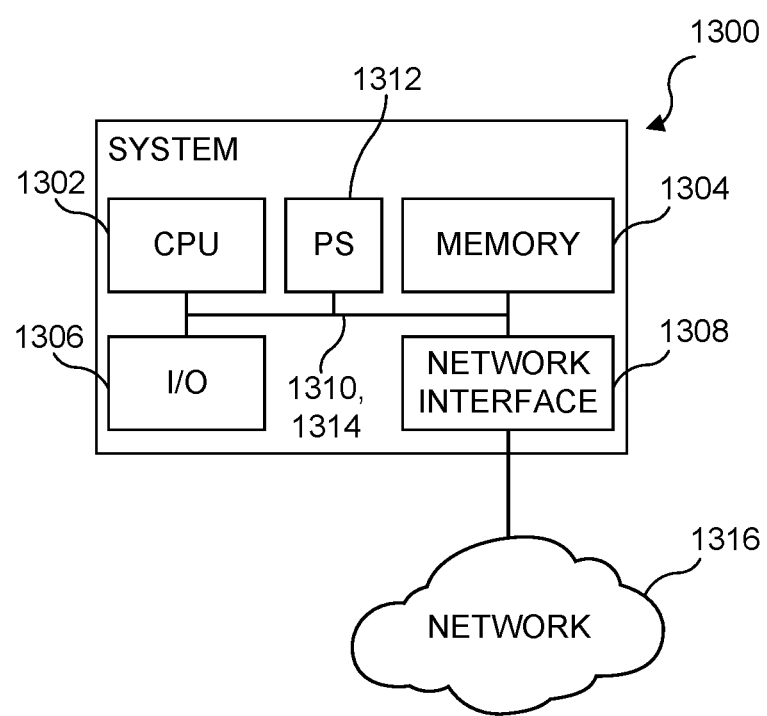
FIG. 13 illustrates a diagrammatic view of one embodiment of a system device that may be used within the environment described herein.

Referring now to FIG. 13, one embodiment of a system device 1300 is illustrated. The system device 1300 is one possible example of a device used by a user such as the user device described herein, the employee management device, or the admin device/server. Embodiments include cellular telephones (including smart phones), personal digital assistants (PDAs), netbooks, tablets, laptops, desktops, workstations, telepresence consoles, and any other computing device that can communicate with another computing device using a wireless and/or wireline communication link. Such communications may be direct (e.g., via a peer-to-peer network, an ad hoc network, or using a direct connection), indirect, such as through a server or other proxy (e.g., in a client-server model), or may use a combination of direct and indirect communications. It is understood that the device may be implemented in many different ways and by many different types of systems, and may be customized as needed to operate within a particular environment.

The system 1300 may include a controller (e.g., a central processing unit ("CPU")) 1302, a memory unit 1304, an input/output ("I/O") device 1306, and a network interface 1308. The components 1302, 1304, 1306, and 1308 are interconnected by a transport system (e.g., a bus) 1310. A power supply (PS) 1312 may provide power to components of the computer system 1300, such as the CPU 1302 and memory unit 1304, via a power system 1314 (which is illustrated with the transport system 1310 but may be different). It is understood that the system 1300 may be differently configured and that each of the listed components may actually represent several different components. For example, the CPU 1302 may actually represent a multi-processor or a distributed processing system; the memory unit 1304 may include different levels of cache memory, main memory, hard disks, and remote storage locations; the I/O device 1306 may include monitors, keyboards, and the like; and the network interface 1308 may include one or more network cards providing one or more wired and/or wireless connections to a network 1316. Therefore, a wide range of flexibility is anticipated in the configuration of the computer system 1300.

The system 1300 may use any operating system (or multiple operating systems), including various versions of operating systems provided by Microsoft (such as WINDOWS), Apple (such as Mac OS X), UNIX, and LINUX, and may include operating systems specifically developed for handheld devices such as iOS or Android, personal computers, servers, and embedded devices depending on the use of the system 1300. The operating system, as well as other instructions, may be stored in the memory unit 1304 and executed by the processor 1302. For example, the memory unit 1304 may include instructions for performing some or all of the methods described herein.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:
1. A method for employee biometric tracking, comprising:
providing to a user a plurality of wearable devices capable of being connected to the user;
establishing a predictive engine based on fatigue patterns at a remote management system;

establishing a wireless connection between the plurality of wearable devices and a mobile device;
collecting by the plurality of wearable devices a plurality of biometric data from the user including blink rate data, head acceleration data, and sleep data, wherein the sleep data includes REM sleep data;
creating and updating over time an electronic log, wherein the electronic log includes a plurality of states of the user each mapped to one or more time periods and each mapped to one or more of the plurality of biometric data, the plurality of states including:
 a sleep state corresponding to when the user is actively sleeping,
 an on state corresponding to when the user is working but not driving,
 an off state in which the user is not working, and
 a drive state corresponding to when the user is driving or performing another task;
receiving by an application stored on the mobile device the plurality of biometric data;
inputting, into the predictive engine, biometric data selected from the plurality of biometric data;
adjusting a predicted employee behavior pattern based on the sleep data received over time for an employee, including:
 adjusting an under-prediction by the predictive engine by gradually increasing a predicted number of awake hours at periodic intervals, wherein the under-prediction indicates that the predicted number of awake hours for the user is predicted based on tracked REM sleep hours for the user and is predicted less than a number of actual awake hours of the user, and
 adjusting an over-prediction by the predictive engine by gradually decreasing the predicted number of awake hours at periodic intervals, wherein the over-prediction indicates that the predicted number of awake hours for the user is predicted based on the tracked REM sleep hours for the user and is predicted greater than the number of actual awake hours of the user;
retraining the predictive engine, in response to and based on the adjusted predicted employee behavior pattern, to update the fatigue patterns;
determining, by the predictive engine in response to the biometric data and based on the fatigue patterns, whether the user is at, or soon will be at, a fatigue alert level;
creating an alert signal;
displaying the alert signal to the user and to the remote management system;
storing, by the remote management system, an alert event, wherein the alert event includes information comprising biometric data that triggered the alert signal; and
updating the fatigue patterns of the predictive engine for the user based on the alert event.

2. The method of claim 1, wherein displaying the alert signal to the user and to the remote management system further includes simultaneously displaying the alert signal to the remote management system.

3. The method of claim 1, further comprising storing, by the application, the alert event.

4. The method of claim 1, further comprising training the predictive engine using the biometric data that triggered the alert signal and the fatigue patterns for the user, wherein the predictive engine is trained on data specific to the user.

5. The method of claim 1, further comprising producing by the mobile device an audible alert simultaneously with displaying the alert signal to the user.

6. The method of claim 5, further comprising producing by the mobile device a vibratory alert simultaneously with displaying the alert signal to the user.

7. The method of claim 1, further comprising producing by the mobile device a vibratory alert simultaneously with displaying the alert signal to the user.

8. The method of claim 1, wherein the plurality of biometric data includes at least one biometric data type.

9. The method of claim 8, wherein the fatigue alert level is a threshold value associated with the at least one biometric data type.

10. The method of claim 1, wherein the predictive engine is a neural network.

11. A system for employee biometric tracking, comprising:
 at least one processor; and
 a memory coupled to the at least one processor, the memory including computer executable instructions that cause the at least one processor to:
  establish a predictive engine based on fatigue patterns at a remote management system;
  establish a wireless connection to a plurality of wearable devices;
  receive a plurality of biometric data from the plurality of wearable devices connected to a user, wherein the plurality of biometric data includes blink rate data, head acceleration data, and sleep data, wherein the sleep data includes REM sleep data;
  create and update over time an electronic log, wherein the electronic log includes a plurality of states of the user each mapped to one or more time periods and each mapped to one or more of the plurality of biometric data, the plurality of states including:
   a sleep state corresponding to when the user is actively sleeping,
   an on state corresponding to when the user is working but not driving,
   an off state in which the user is not working, and
   a drive state corresponding to when the user is driving or performing another task;
  input, into the predictive engine, biometric data selected from the plurality of biometric data;
  adjust a predicted employee behavior pattern based on the sleep data received over time for an employee, including:
   adjust an under-prediction by the predictive engine by gradually increasing a predicted number of awake hours at periodic intervals, wherein the under-prediction indicates that the predicted number of awake hours for the user is predicted based on tracked REM sleep hours for the user and is predicted less than a number of actual awake hours of the user, and
   adjust an over-prediction by the predictive engine by gradually decreasing the predicted number of awake hours at periodic intervals, wherein the over-prediction indicates that the predicted number of awake hours for the user is predicted based on the tracked REM sleep hours for the user and is predicted greater than the number of actual awake hours of the user;
  retrain the predictive engine, in response to and based on the adjusted predicted employee behavior pattern, to update the fatigue patterns;

determine, by the predictive engine in response to the biometric data and based on the fatigue patterns, whether the user is at, or soon will be at, a fatigue alert level;

create an alert signal;

display the alert signal to the user and to the remote management system;

store, at the remote management system, an alert event, wherein the alert event includes information comprising biometric data that triggered the alert signal; and update the fatigue patterns of the predictive engine for the user based on the alert event.

12. The system of claim 11, wherein displaying the alert signal to the user and to the remote management system further includes simultaneously displaying the alert signal to the remote management system.

13. The system of claim 11, wherein the memory further includes computer executable instructions that cause the at least one processor to store, in a local application, the alert event.

14. The system of claim 11, wherein the memory further includes computer executable instructions that cause the at least one processor to train the predictive engine using the biometric data that triggered the alert signal and the fatigue patterns for the user, wherein the predictive engine is trained on data specific to the user.

15. The system of claim 11, wherein the memory further includes computer executable instructions that cause the at least one processor to produce an audible alert simultaneously with displaying the alert signal to the user.

16. The system of claim 15, wherein the memory further includes computer executable instructions that cause the at least one processor to produce a vibratory alert simultaneously with displaying the alert signal to the user.

17. The system of claim 11, wherein the memory further includes computer executable instructions that cause the at least one processor to produce a vibratory alert simultaneously with displaying the alert signal to the user.

18. The system of claim 11, wherein the plurality of biometric data includes at least one biometric data type.

19. The system of claim 18, wherein the fatigue alert level is a threshold value associated with the at least one biometric data type.

20. The system of claim 11, wherein the predictive engine is a neural network.

\* \* \* \* \*